(12) United States Patent
Wada

(10) Patent No.: US 7,572,358 B2
(45) Date of Patent: Aug. 11, 2009

(54) ELECTROPHORESIS METHOD AND APPARATUS

(75) Inventor: Akira Wada, 16-15, Hieidaira 3-chome, Otsu-shi, Shiga (JP) 520-0016

(73) Assignee: Akira Wada, Shiga (JP)

( * ) Notice: Subject to any disclaimer, the term of this patent is extended or adjusted under 35 U.S.C. 154(b) by 842 days.

(21) Appl. No.: 10/982,567

(22) Filed: Nov. 5, 2004

(65) Prior Publication Data

US 2005/0139471 A1 Jun. 30, 2005

(30) Foreign Application Priority Data

Dec. 24, 2003 (JP) ............................. 2003-427721

(51) Int. Cl.
*G01N 33/559* (2006.01)
*G01N 27/00* (2006.01)
(52) U.S. Cl. .................. 204/621; 204/606; 204/616; 204/618; 204/456; 204/466
(58) Field of Classification Search ........................ None
See application file for complete search history.

(56) References Cited

U.S. PATENT DOCUMENTS

| | | | | |
|---|---|---|---|---|
| 4,613,419 | A | * | 9/1986 | Dehming ................ 204/613 |
| 5,888,364 | A | * | 3/1999 | Schuette ................. 204/466 |
| 6,406,602 | B1 | * | 6/2002 | Cahill et al. ............ 204/456 |
| 6,942,775 | B1 | * | 9/2005 | Fox ........................ 204/467 |

FOREIGN PATENT DOCUMENTS

| | | |
|---|---|---|
| JP | 6-41933 B | 6/1994 |
| JP | 6-41934 B | 6/1994 |
| WO | WO-96/04549 A1 | 2/1996 |
| WO | WO-97/31263 A1 | 8/1997 |

OTHER PUBLICATIONS

Analysis of *Escherichia coli* Ribosomal Proteins by an Improved Two Dimensional Gel Electrophoresis. I. Detection of Four New Proteins, Akira Wada, vol. 100, p1583-p1594, Journal of Biochemistry, 1986.
Analysis of *Escherichia coli* Ribosomal Proteins by an Improved Two Dimensional Gel Electrophoresis. II. Characterization of Four New Proteins, Akira Wada, vol. 100, p1595-p1605, Journal of Chemistry, 1986.

(Continued)

*Primary Examiner*—Kaj K Olsen
*Assistant Examiner*—Kourtney R Salzman
(74) *Attorney, Agent, or Firm*—Darby & Darby P.C.

(57) ABSTRACT

A first dimension electrophoresis apparatus of vertical type with a gel container 2 having a plurality of rectangular rod-shaped gel chambers is provided. The rod-type gels surrounded with non-conductive material plates are arranged in parallel, an upper open end of the gel container 2 is placed tightly into an upper buffer reservoir 4 and the lower open end thereof is placed tightly into a lower buffer reservoir 1. The gel container 2 and the main parts of the first buffer reservoir 4 and the lower buffer reservoir 1 are sunk in a cooling reservoir 5 filled with cooling liquid. The lower buffer reservoir has a panel portion 1b which is bent upward to penetrate the cooling reservoir. Outlet conductors thereof extend from each of the reservoirs and are insulated physically and electrically from the cooling liquid. As a result, the outer surface of the gel container can directly contact with the cooling liquid.

4 Claims, 23 Drawing Sheets
(5 of 23 Drawing Sheet(s) Filed in Color)

OTHER PUBLICATIONS

Structure and probable genetic location of a "ribosome modulation factor" associated with 100S ribosomes in stationary-phase *Escherochia coli* cells, Akira Wada, et. al., Proceedings of National Academy of Science, U.S.A, vol. 87, p2657-p2661, Apr. 1990.

Two proteins, YfiA and YhbH, associated with resting ribosomes in stationary phase *Escherichia coli*, Yasushi Maki, et. al., Genes to Cells, 5, p956-p974 (2000).

Characterization of teh ribosomal proteins of the amitochondriate protist, *Giardia lamblia*, Tetsurou Shirakura, et. al., Molecular and Biochemical Parasitology, 112, p153-p156 (2001).

* cited by examiner

A

B

A

B

A

B

Total 65

ELECTROPHORESIS METHOD AND APPARATUS

BACKGROUND OF THE INVENTION

Incorporation by Reference

The present application claims priority under 35 U.S.C. §119 to Japanese Patent Application No. 2003-427721 filed on Dec. 24, 2003. The content of the application is incorporated herein by reference in its entirety.

1. Field of the Invention

The present invention relates to a method of electrophoresis and an apparatus for implementing this method, for using in separation, assay or structural analysis of samples. The present invention provides a method and an apparatus for assaying, in particular, protein samples with high accuracy.

2. Related Background Art

In the prior art, a method of two-dimensional electrophoresis included electrically migrating a sample in a first dimension gel, placing the resulting first dimension gel column at the upper end of a second dimension gel, and further electrophoresis. For the first dimension and second dimension gels, polyacrylamide is used. When conducting separation analysis of E. coli ribosomal protein, the sample protein is added as a solution to the first dimension gel in column type. By its migration, the components separate (first-dimension separation). The columnar gel which is fixed in this condition is placed on the upper end of the second dimension gel, and the second dimensional electrophoresis is conducted.

The inventor has previously developed a two dimensional electrophoresis method (for example, see Japanese Patent Number 191894, Akira. Wada), wherein: a zero-dimension sample gel is created by concentrating the sample by electrophoresis in a pre-treatment bar-shaped gel; said sample gel is inserted at a desired position which is cut out in the first dimension gel, and first dimension electrophoresis is conducted; the first dimension gel in which protein has been separated is placed on the upper end of the second dimension gel, and electrophoresis is conducted.

In this method for two dimensional electrophoresis which includes creating a zero-dimension sample gel, the sample is concentrated so as to avoid having individual protein molecules in the sample encounter free radicals. This results in a more effective first-dimension migration and second dimension migration. In this situation, the pre-treatment bar-shaped gel such as zero-dimension sample gel and the first dimension gel have a square cross-section. This results in the zero-dimension sample gel and the first dimension sample gel each being attached without any gap to the first dimension gel and second dimension gel respectively. This solves a problem of previous methods in which the first dimension gel is prepared within a cylindrical tube and where disturbances in the migration can result due to gaps on either side of the joining surface.

However, in order to improve the analytical accuracy, during the processes of the creation of the first and the second dimension gel and the first and the second dimension electrophorisises, the temperature within the gel chamber must be held at the temperature which is closest to the most stable temperature for an aqueous gel (4-10 degrees C.). This keeps the diffusion due to temperature of the protein molecules at a minimum. In the prior art, the temperature control of the gel chamber was conducted through the storage solution in the buffer reservoir which connects with both ends of the gel. This was not adequate.

For example, Chen, Stephen, C. and Yongson, Acselson, Ulvan, etc. have tried to improve the analytical accuracy by directly cooling a gel part only (WO 97/31263 and Japanese Laid-Open Patent Publication No. H10-503594). However such direct cooling of only a gel part is inevitably insufficient for maintaining of temperature for cooling a gel chamber, because a joule heating that accompanies to electrophoresis are conducted to the gel chamber directly from non-cooled spaces through buffer solution.

SUMMARY OF THE INVENTION

The first object of the present invention is to provide an apparatus construction that will accurately control the Gel container with buffer chamber at a most stable temperature for an aqueous gel (around 4-10 degrees C.) during the processes of the first dimension gel and second dimension electrophoresis. This keeps the diffusion due to temperature of the protein molecules at a minimum.

An embodiment of the first means for solving the above recited problem is an electrophoresis method and apparatus. The apparatus includes a gel container wherein a plate-type gel is surrounded with non-conductive material plates. An open end of the gel container is placed into the first buffer reservoir and the opposite open end thereof is placed into the second buffer reservoir, and the connected parts between the gel container and the first and the second buffer reservoirs maintain a liquid tight sealing structure. In implementing an electrophoresis procedure, the gel container and the main parts of the first and the second buffer reservoirs are sunk in a cooling reservoir in which cooling liquid is filled.

In another embodiment, the above recited means are embodied in an electrophoresis apparatus of vertical type. An upper open end of the gel container is connected to the upper buffer reservoir, and an lower open end thereof is connected to the lower buffer reservoir while maintaining a liquid tight sealing structure. The gel container and the main parts of the first and the second buffer reservoirs are sunk in a cooling reservoir in which cooling liquid is filled, the lower buffer reservoir has a panel portion which is bent upward to penetrate the cooling reservoir and an upper end of the panel portion (the level of the surface of buffer in the second buffer reservoir) is essentially at the same level as an upper end of the upper buffer reservoir (the level of the surface of buffer in the first buffer. In another embodiment of an electrophoresis apparatus of the present invention, a gel container has a horizontal structure, and an open end of the gel container is connected to the first buffer reservoir and the opposite open end thereof is connected to the second buffer reservoir, with both connected parts maintaining a liquid tight sealing structure. The gel container and the main parts of the first and the second buffer reservoirs are sunk in a cooling reservoir in which cooling liquid is filled.

Another embodiment of an electrophoresis apparatus of the invention has a gel container which forms at least one row of gel chambers and buffer reservoirs which have openings (container insertion openings) respectively through the gel chamber of the gel container One end and the other end of the gel container are placed in the respective reservoirs while maintaining a liquid tight sealing structure. The gel container and the main parts of both buffer reservoirs are sunk in a cooling liquid, and the buffer reservoirs are equipped with electrode outlet conductors for supplying electrophoresis voltage which extend from each of the reservoirs and are insulated physically and electrically from the cooling liquid.

In another embodiment of an electrophoresis apparatus of this invention is a vertical-type one which has the construction recited above. The lower buffer reservoir has a panel portion which is bent upward from a back end of a main area which is in communication with lower end opening of the gel chambers; an upper end of the panel portion is essentially at the same level as an upper end of the upper buffer reservoir; the panel portion is the only opening for the lower buffer reservoir; with the exception of the upper end of the upper buffer chamber and the upper end of the panel portion of the lower buffer reservoir, the entire apparatus can be essentially immersed in cooling liquid.

Still another embodiment of an electrophoresis apparatus of this invention has an open row at a middle portion of the gel container. The middle portion connects to one part of each gel chamber. This serves an opening for inserting the concentrated sample gel piece. A cover plate of the open row (a window cover plate) is equipped with a plug row for tightly closing the open row after insertion of the sample gel piece.

In the inventions recited above, a liquid tight sealing structure between the gel container and the buffer reservoirs and the structure of the buffer reservoirs for preventing invasion of cooling liquid can be attained by sealing the liquid-invasion susceptible portions in the apparatus. The structure can be crossing parts between the gel container and the gel container insertion openings of the buffer reservoirs with a sealing agent, etc.

In another embodiment, the electrophoresis method includes maintaining a tight seal on the connected parts between the gel container and the first and the second buffer reservoirs, inserting a sample gel at a desired portion in the gel chamber held between gel container plates, disposing the first and the second buffer reservoirs in the cooling reservoir which is filled with cooling liquid, and maintaining the temperature of the cooling liquid during the electrophoresis is at a range of 4-10° C.

In implementing an embodiment of the electrophoresis method of this invention in a first dimension, a first dimension electrophoresis apparatus is used. The first dimension electrophoresis apparatus, for example, has a gel container which forms at least one row of rod-shaped gel chamber, an opening at a middle part of the container to the inner gel chamber and a cover plate for tightly closing the opening. The first dimension gel is cut out at the opening portion of the gel container in the gel chamber of which the first dimension gel is made, and a sample gel is inserted into the cut portion, and the opening is closed liquid tightly with said cover plate. After that, this container, the first and the second buffer reservoirs are sunk in the cooling reservoir which is filled with cooling liquid, and the temperature of the cooling liquid during the electrophoresis is maintained at a range of 4-10° C.

In implementing an embodiment of the electrophoresis method of this invention in a second dimension, the second dimension electrophoresis apparatus is used. The second dimension electrophoresis apparatus, for example, has a gel container which forms at least one flat gel chamber. A square-shaped gel as a result of the first dimension gel electrophoresis is placed as a sample gel on the upper end of the gel container in which the second dimension gel has been made, that is, on the second dimension gel. Then, the sample gel on the second dimension gel is covered with, for example, a gauze, in order to avoid separation of the sample gel from the second dimension gel into the buffer liquid. After that, this container, the first and the second buffer reservoirs are sunk in the cooling reservoir which is filled with cooling liquid, and the temperature of the cooling liquid during the electrophoresis is maintained at a range of 4-10° C.

The electrophoresis method and apparatus for implementing this invention can be used in any of separation assay procedures which require a low temperature condition including the O'Farrell method and the immobilized pH gradient method (for example, a separation assay of proteins in a serum, etc.). By concentrating samples as a pre-treatment by means of the Radical-free and Highly Reducing (RFHR) method recited below for concentrating all proteins regardless of their isoelectric points, more superior assay results can be attained.

A procedure of the RFHR method as a pre-treatment is the following: by conducting electrophoresis of a sample at a pH of 5.5 in a pre-treatment rod-shaped gel with a buffer solution containing K+ as a leading ion and glycine and cysteine as trailing ions, a zero-dimensional sample gel, in which proteins of every isoelectric point of pH approximately 4 or higher is concentrated in the negative electrode direction, is created. This sample gel is inserted into the first dimension gel at the desired position, and first dimension electrophoresis is conducted. With this, a first dimension separated gel is prepared, and this is further electrophoresed by placing on the upper end of a second dimension gel.

Another pre-treatment procedure of the RFHR method is the following: for the creation of a zero-dimensional sample gel, electrophoresis of a sample is conducted at a pH of 3.0 in a pre-treatment rod-shaped gel with a buffer solution containing K+ as a leading ion and glutamic acid as a trailing ion. With this, a zero-dimensional sample gel, in which proteins of all different isoelectric points are concentrated in the negative electrode direction, is created. Another pre-treatment procedure of the RFHR method is the following: for the creation of a zero-dimensional sample gel, electrophoresis of a sample is conducted at a pH of 10.6 in a pre-treatment rod-shaped gel with a buffer solution containing Cl− as a leading ion and arginine as a trailing ion. With this, a zero-dimension sample gel, in which proteins with isoelectric points of pH 11 or less are concentrated in the positive electrode direction, is created.

Effects of this Invention:

The electrophoresis method and the apparatus for implementing this invention can maintain an electrophoresis gel cool more accurately and more reliably without omission than those where only a gel part is cooled, by sinking the whole apparatus including buffer reservoirs in cooling liquid and by maintaining the liquid at a range of temperature. Therefore, they are in themselves extremely effective for proteomics, such as for complicated analysis of high molecular weight components, for example, proteins, hormone, etc. Besides, when samples are pre-treated or pre-concentrated in the RFHR electrophoresis method recited above, more superior effects can be attained.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

DESCRIPTION OF THE PREFERED EMBODIMENTS

Figure 1:
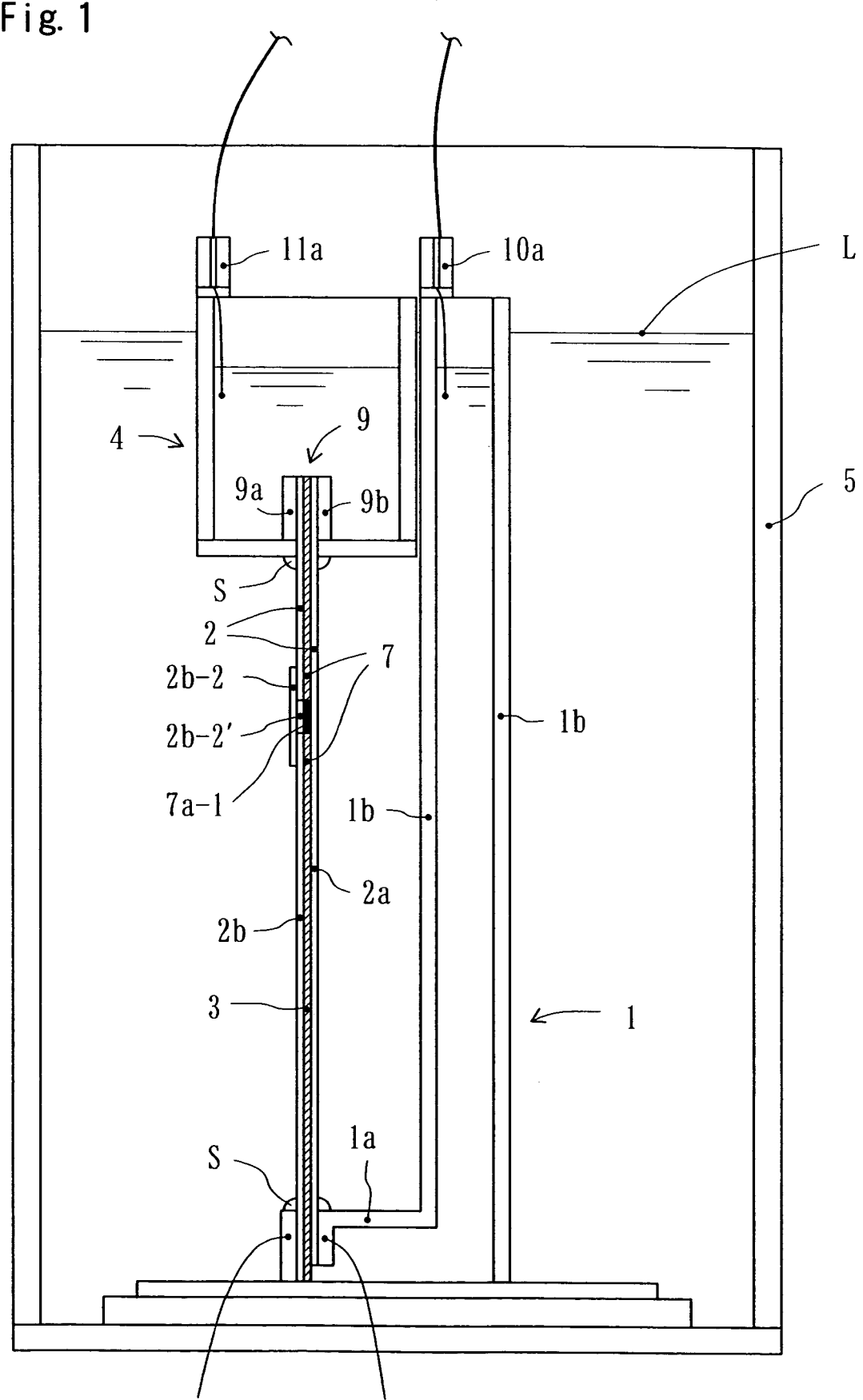
FIG. 1 is a lateral cross-section showing an example (a vertical-type) of a first dimension electrophoresis apparatus of this.

FIG. 1 shows a first example (a vertical type) of a first dimension electrophoresis apparatus wherein a sample piece 7a-1 (zero dimension sample) is inserted into the middle portion of the first dimension gel 7. There is a lower buffer reservoir 1, a gel container 2 in which a plurality of upright, rectangular rod-shaped gel chambers 3 are arranged in parallel, and an upper buffer reservoir 4. Lower buffer reservoir 1 and upper buffer reservoir 4 are both formed from plastic which is corrosion-resistant and which has excellent electrical insulation and mechanical strength. However, only first dimension gel container 2 is preferably formed from glass with high heat conductivity. Lower buffer reservoir 1 has a panel portion 1b which is bent upward from the back end of main area 1a which connects with the lower end opening of gel chamber 3. The upper end of panel portion 1b is essentially at the same level as the upper end of upper buffer reservoir 4. During use, panel portion 1b exists as the only opening for the lower buffer reservoir. As a result, except for the upper end of upper buffer reservoir 4 and the upper end of panel portion 1b of the lower buffer reservoir, essentially the entire apparatus can be submerged in a cooling liquid within a cooling reservoir 5 which is hypothetically drawn. L is a surface of cooling liquid. The cooling reservoir 5 has an opening for pouring cooling liquid at the position on its one side wall where the middle portion of one side of sunk gel container faces (the opening is not shown; See 30 in FIG. 15) and an opening for discharging cooling liquid at the corresponding position on its opposite side wall(the opening is also not shown; See 31 in FIG. 15). The openings for pouring and discharging cooling liquid are connected respectively with pipes through to a tank for cooling liquid(See 32 and 33 in FIG. 15). Because of this structure, cooling liquid is circulated from one side to another side of the gel container, and as a result, the temperature of the gel container and the buffer reservoirs can be maintained to be cool more accurately and more reliably.

The lower end of gel container 2 is inserted and supported into the opening 6(FIG. 2B) between a protruding front end wall 6a of lower buffer reservoir 1 and a hanging wall 6b which is slightly before the front end wall. The lower end of gel container plate 2a, which forms gel container 2, ends at the same level as the lower end of hanging wall 6b. The lower end of cover plate 2b is supported by the reservoir lower surface. As a result, over the entire length of the lower end of gel 7 between plates 2a and 2b, there is a space between gel 7 and the reservoir bottom surface, and gel 7 is in contact with buffer solution inside lower buffer reservoir 1. In addition, the upper end of gel container 2 is inserted and affixed to container insertion opening 9 in the middle of upper buffer reservoir 4. The upper end opening of gel chamber 3 is in communication with the liquid phase of upper buffer reservoir 4.

Figure 2:
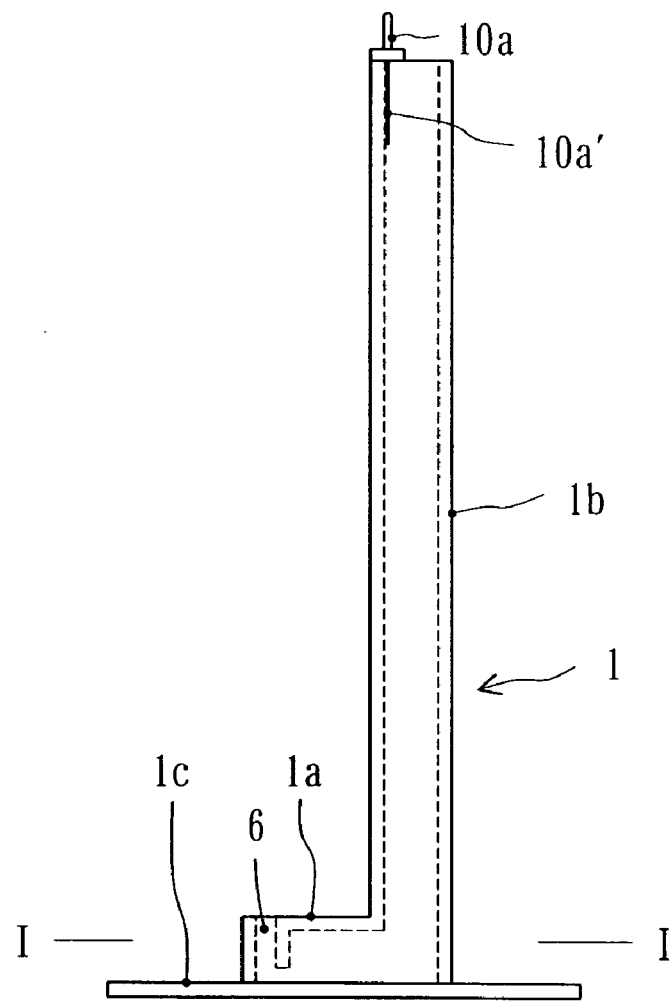
FIG. 2 is a side view A and a partial broken out plan view B of a lower buffer reservoir of the first dimension electrophoresis apparatus of FIG. 1.
Figure 2:
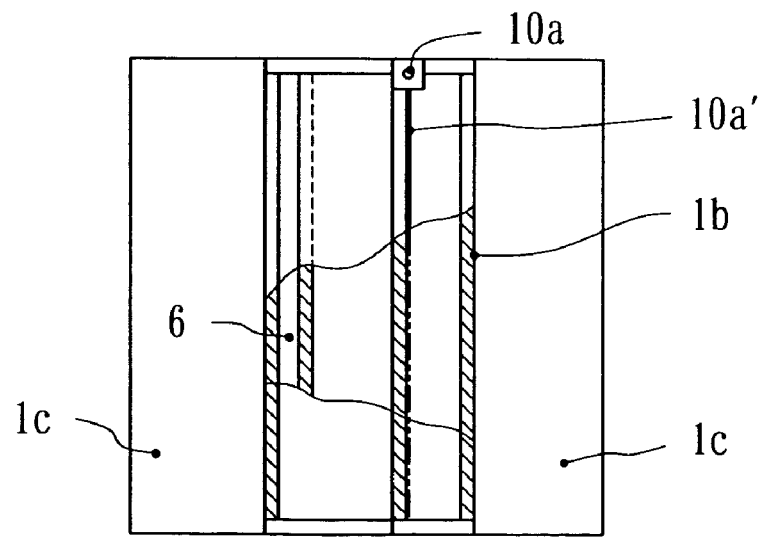

FIG. 2 is a side view A of lower buffer reservoir 1 and a partial broken-out plan view B including cross-section view along line I-I of side view FIG. 2. Bottom plate 1c protrudes out from both the front end of lower buffer reservoir main element 1a and the back end of panel portion 1b and stably supports lower buffer reservoir 1, gel container 2, and upper buffer reservoir 4. An electrode terminal 10a of lower buffer reservoir 1 is attached to the upper end of panel portion 1b. Terminal 10a is connected to a platinum wire 10a' which is immersed in the buffer solution inside panel portion 1b. With platinum wire 10a', the lower end, which is hanging approximately 20 mm from the upper end of panel portion 1b, is bent so that it is horizontal and is spread along the entire length of the panel portion (see plan view 6B).

Figure 3:
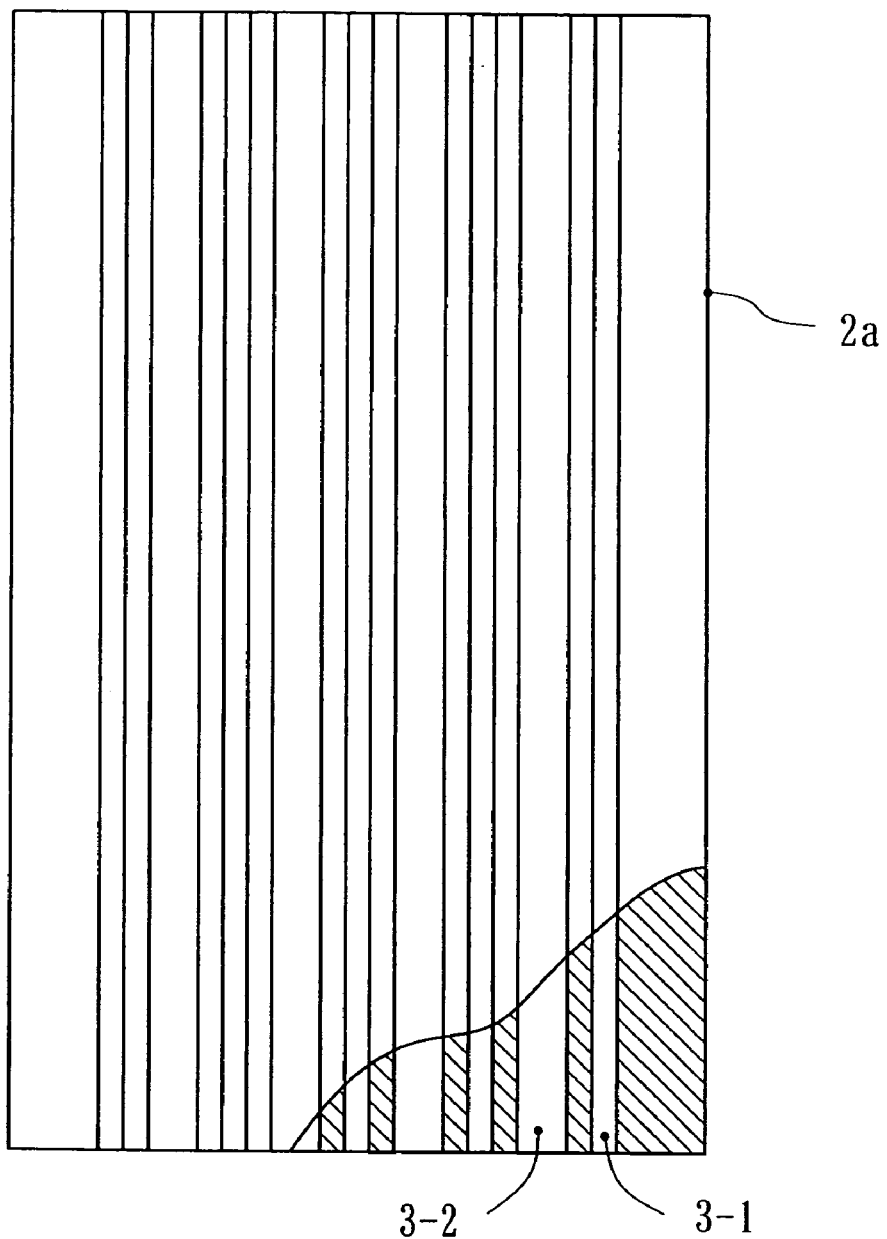
FIG. 3 is a front view A and a bottom side view B of a gel container plate of the first dimension electrophoresis apparatus of FIG. 1.
Figure 3:
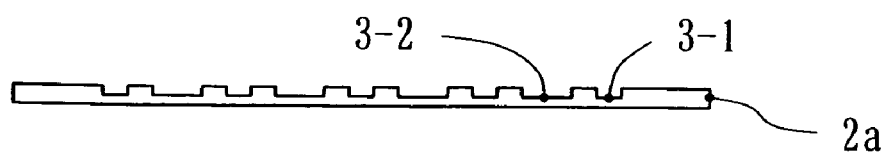

FIG. 3 is a plan view A and a side view B of gel container plate 2a which forms first dimension gel container 2. Container plate 2a has standard narrow gel grooves 3-1 (in this case, a width of 5 mm) and wide gel grooves 3-2 having twice the width. Both have a depth of 2 mm, and the narrow and wide gel grooves are arranged in an alternating manner. As shown in FIGS. 4A, B, and C, an upper cover plate 2*b*-1, a window cover plate 2*b*-2, and a lower cover plate 2*b*-3 are placed on the groove surface side of container plate 2*a*, and parallel gel chambers which are flat and long and narrow are formed. For the electrophoresis apparatus for creating the first dimension gel, when cover plate 2*b* is placed opposite container plate 2*a*, a space wide enough for window cap 2*b*-2' is left open between upper cover plate 2*b*-1 and lower cover plate 2*b*-3. This space becomes the insertion opening into gel chamber 3 for the zero dimension sample piece. After its insertion, window cap 2*b*-2' of window plate 2*b*-2 is placed in this space (insertion opening). The main body of window plate 2*b*-2 (the outer plate) is placed on the outer surface of upper cover plate 2*b*-1 and lower cover plate 2*b*-3 (see FIG. 1).

Figure 5:
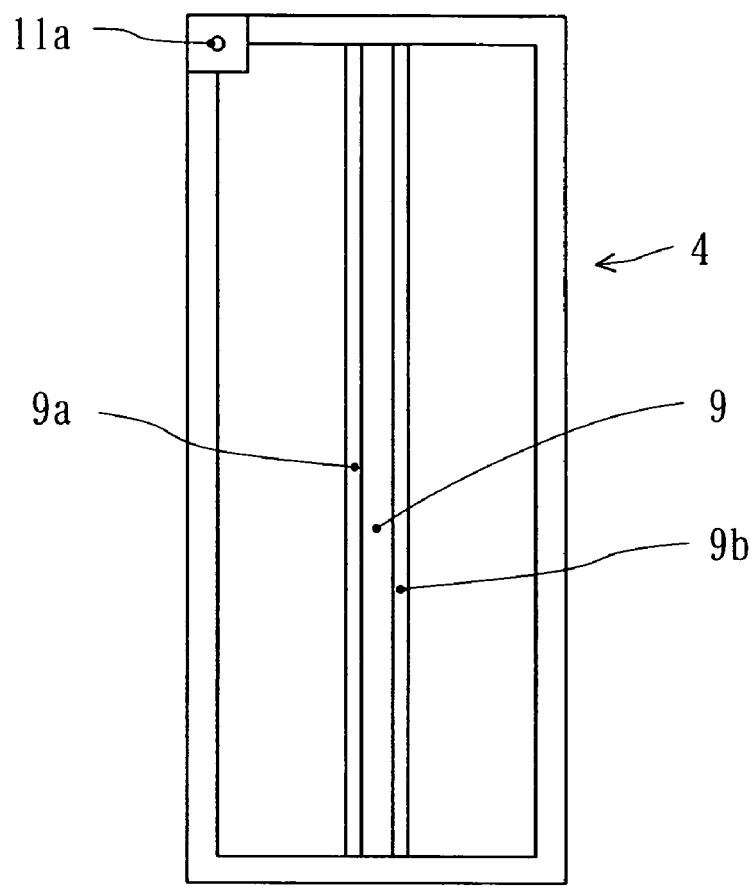
FIG. 5 is a plan view A and a side view B of an upper reservoir of the first-dimension electrophoresis apparatus of FIG. 1.
Figure 5:
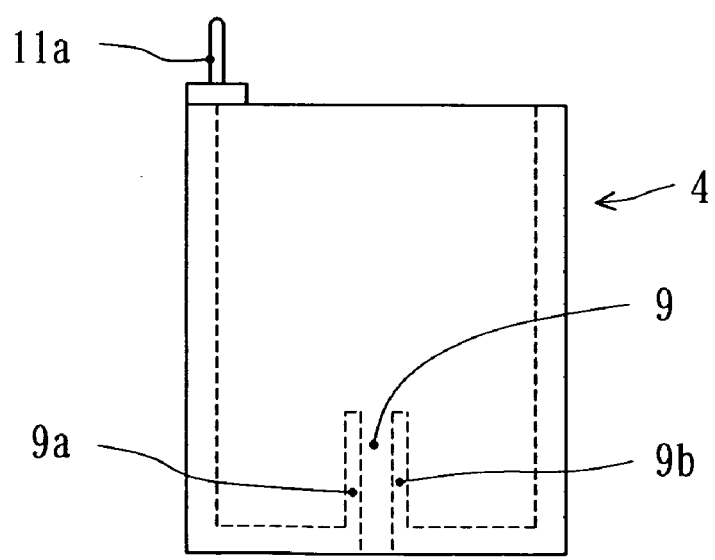

FIG. 5 is a plan view A and a side view B of first dimension upper buffer reservoir 4. Container insertion opening 9, which is in the middle of buffer reservoir 4, is formed between a pair of panels 9*a*, 9*b* which face each other at a constant distance on the bottom surface in the middle of buffer reservoir 4. Panels 9*a*, 9*b* have a suitable height, and they are in contact with the upper end of gel container 2 within the range of this height. As a result, the uppermost position of the gel container for the first dimension electrophoresis apparatus is supported stably. An electrode terminal 11*a* for upper buffer reservoir 4 is attached to the upper end of the corner portion of the side wall and end wall of upper buffer reservoir 4.

In constructing the electrophoresis apparatus recited above, prior to pouring a liquid gel into the gel chamber, the lower end of the gel container 2 is placed into the gel container insertion opening 6 of the lower buffer reservoir 1 and then, a seal agent S is filled into the crossing parts between them and the seal agent S is air-dried and the crossing part is glued and sealed. The crossing part between the upper end of the gel container 2 and the gel container insertion opening of the upper buffer reservoir is glued and sealed in the same way. After completion of sealing, a liquid gel is poured into the gel chamber 3 and it is left for a few minutes to be a gel. As a result, a gel plate is made in the gel chamber. A pre-prepared gel may be packaged into the gel chamber 3 in the gel container 2 in the electrophoresis of this invention wherein the crossing parts of the gel container and both reservoirs have been previously glued and sealed.

Figure 6:
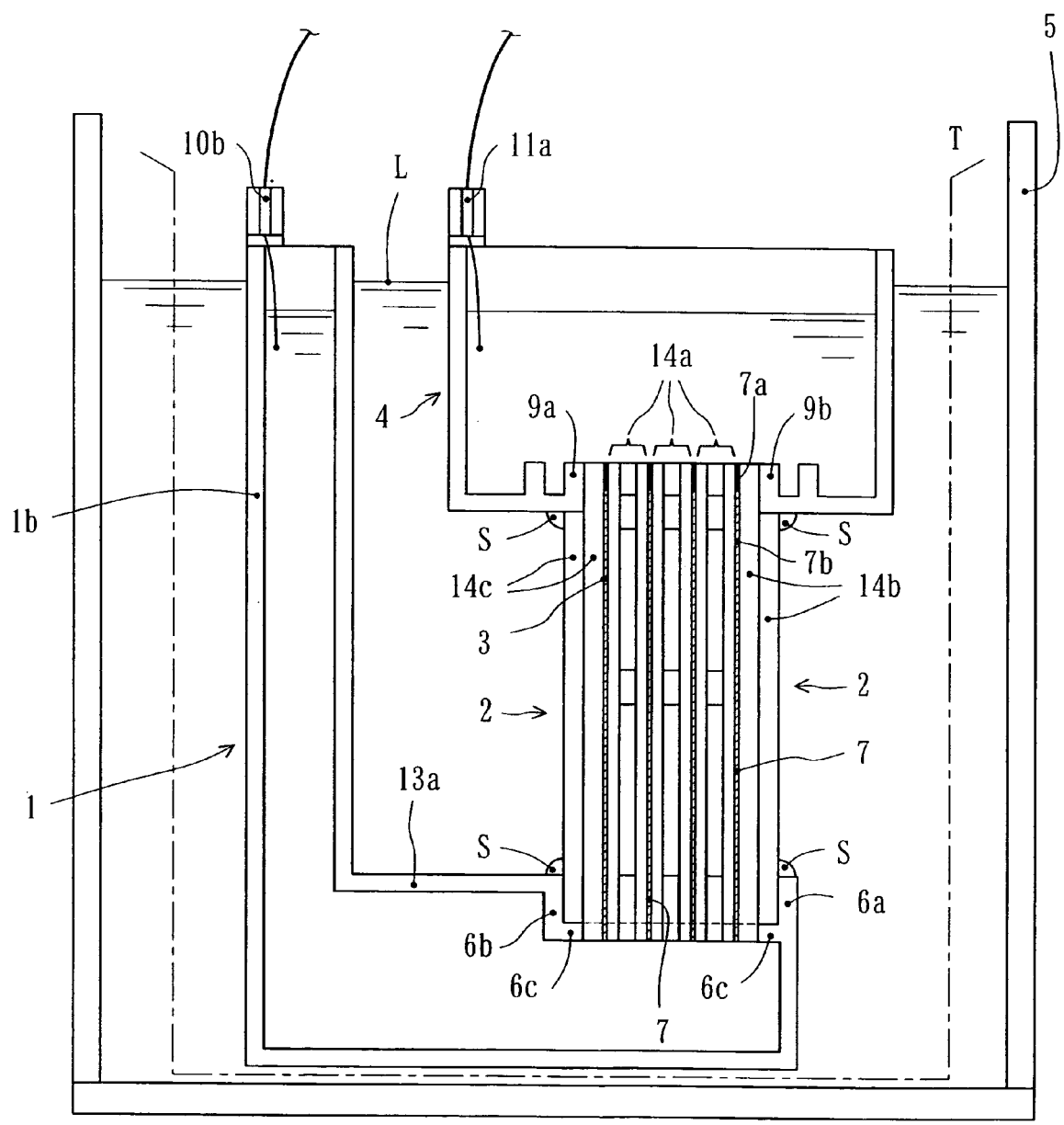
FIG. 6 is a lateral cross-section showing an example (a vertical type) of a second dimension electrophoresis apparatus of this invention.

FIG. 6 is a second dimension electrophoresis apparatus of this invention(a vertical type) in which a first dimension gel 7*a* is placed on top of a second dimension gel 7*b*. There is a lower buffer reservoir 1, a gel container 2, in which a plurality of flat gel chambers 3 are placed upright in an overlapping and parallel condition, and an upper buffer reservoir 4. These are all formed from corrosion resistant plastic with excellent electrical insulation and mechanical strength. Lower buffer reservoir 1 has a panel portion 1*b* which is bent upward. The upper end of panel portion 1*b* is essentially at the same level as the upper end of upper buffer reservoir 4. During use, the upper end of panel portion 1*b* is the only opening that exists for the lower buffer reservoir. Therefore, except for the upper end of upper buffer reservoir 4 and the upper end of panel portion 1*b* of the lower buffer reservoir, essentially the entire apparatus can be immersed in cooling liquid inside cooling reservoir 5. T is a basket-type carrying tray to carry and put in or out the whole apparatus constructed with the upper buffer reservoir 4, the gel container 2, the gel chamber 3 and the lower buffer reservoir 1 from the cooling reservoir. The tray is only for carrying the apparatus and it has a pierced structure which allow cooling liquid to sufficiently penetrate and is never prevent the cooling effect of the method of this invention. L is a surface of cooling liquid. As the first dimension electrophoresis apparatus in FIG. 1, the cooling reservoir has an opening for pouring cooling liquid and an opening for discharging cooling liquid at the positions on its facing side walls where the middle portions of respective sides of sunk gel container face. These openings are connected respectively with pipes through to a tank for cooling liquid. (See FIG. 15)

The lower end of gel container 2, is inserted between a protruding front end wall 6*a* of lower buffer reservoir 1 and a hanging wall 6*b* which forms the insertion opening. The lower end of gel container 2 is supported by the open frame 6*c* formed on the lower end level of hanging wall 6*b*. Gel container 2 is constructed from gel container plate 14*a*, cover plate 14*b*, and container end plate 14*c*. Only the outer perimeter of the lower end of gel container plate 14*a*, cover plate 14*b*, and container end plate 14*c* are supported by open frame 6*c*. As a result, there is a large space between the bottom surface of the reservoir and the lower part of the entire length of the plurality of gels 7 between cover plate 14*b* and container end plate 14*c*, and the lower part of gels 7 are in contact with buffer solution inside lower buffer reservoir 1. In addition, the upper end of gel container 2 is inserted and affixed to a container insertion opening 9 in the middle of upper buffer reservoir 4. The upper end opening of gel chamber 3 is in communication with the liquid phase inside upper buffer reservoir 4.

Figure 7:
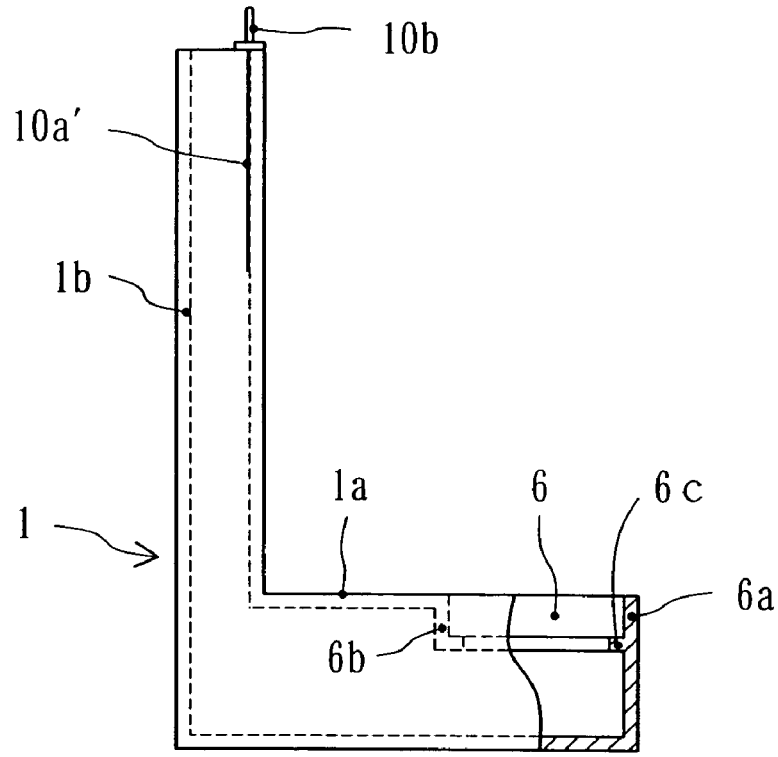
FIG. 7 is a partial broken-out cross-section A and a plan view B of a lower reservoir of the second dimension electrophoresis apparatus of FIG. 6.
Figure 7:
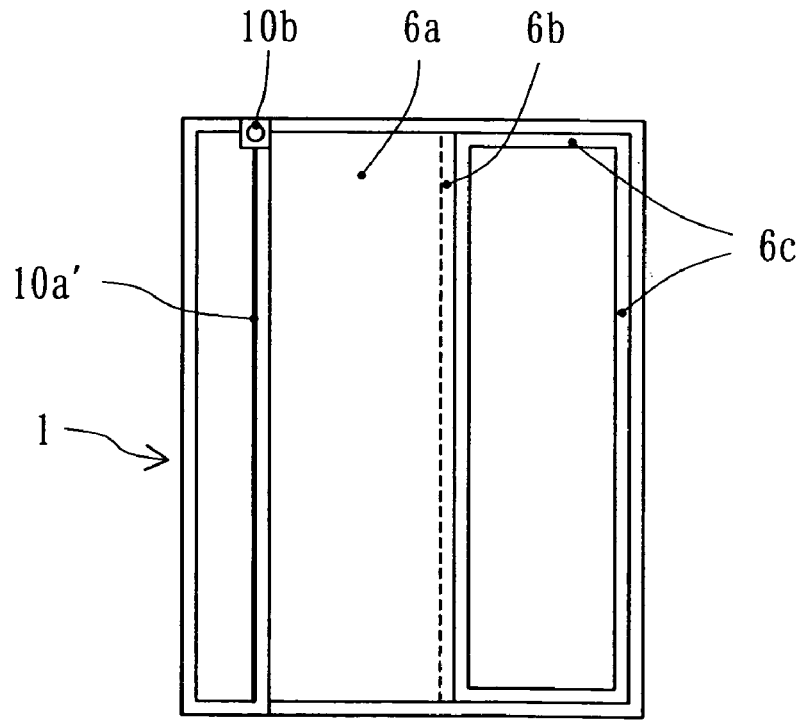

FIG. 7 is a partial broken-out view A and a plan view B of lower buffer reservoir 1. As is clear from the drawing, electrode terminal 10*a* for lower buffer reservoir 1 is attached to the upper end of panel portion 1*b*. Terminal 10*a* is connected to a platinum wire 10*a'* which is immersed in the buffer solution inside panel portion 1*b*. With platinum wire 10*a'*, the lower end, which is hanging approximately 60 mm from the upper end of panel portion 1*b*, is bent so that it is horizontal and is spread along the entire length of the panel portion (see plan view B).

Figure 8:
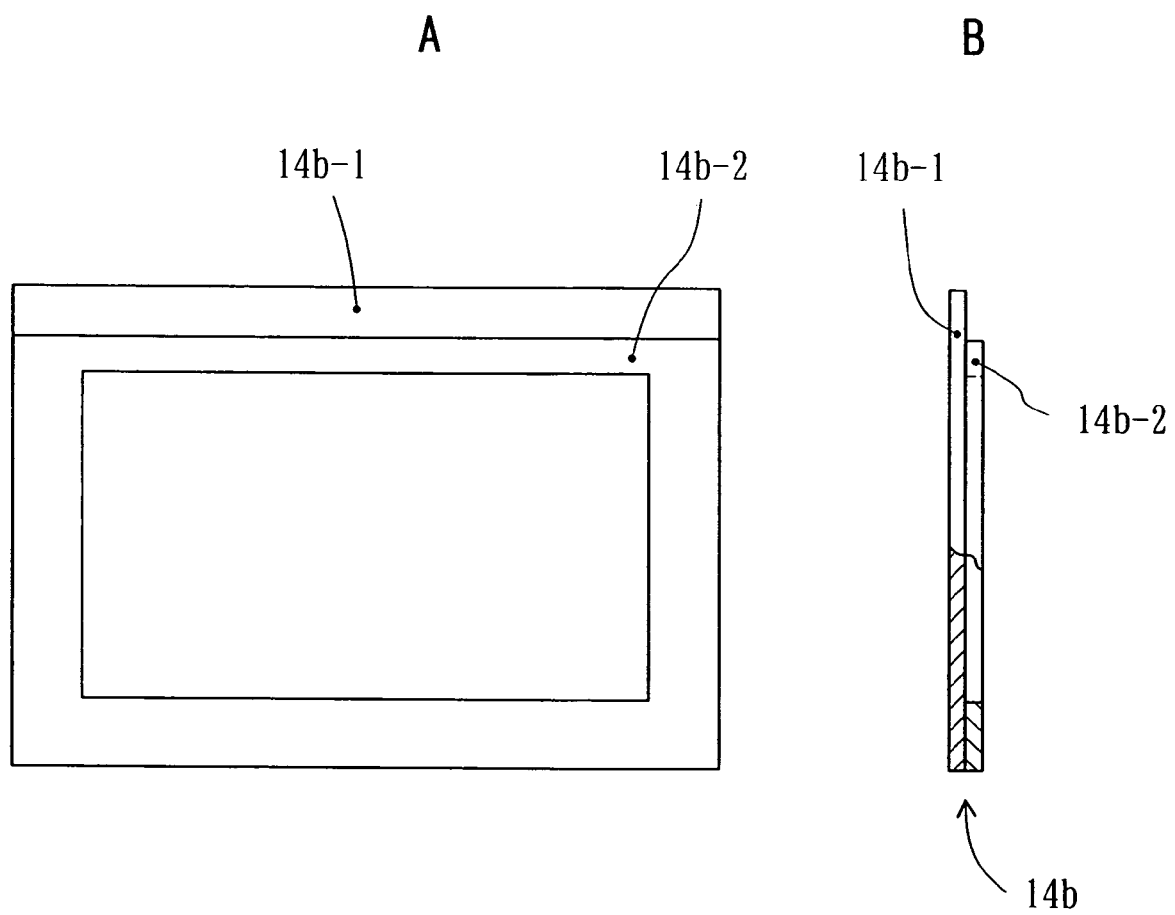
FIG. 8 is a plan view A and a partial broken out right side view B of a cover plate which constructs a second dimension gel container.

In FIG. 6, gel container plate 14*a*, cover plate 14*b*, and container end plate 14*c* construct second dimension gel container 2. FIG. 8 is a plan view A and a partial broken out right view B of cover plate 14*b* which is at the right end of Figure. In FIG. 8, the back surface of cover plate main element 14*b*-1 is in contact with the gel. In front, a cover frame plate 14*b*-2 is attached with the lower end even with the lower end of main element 14*b*-1 or they are formed as a unit. The lower end of cover frame plate 14*b*-2 is supported by open frame 6*c* of the lower buffer reservoir. The upper end of cover frame plate 14*b*-2 is in contact with the lower edge of gel container insertion opening 9 of upper buffer reservoir 4 and plays a part in supporting reservoir 4 and contributes to maintaining the assembly structure of the second dimension electrophoresis apparatus. The inside of the frame of cover frame plate 14*b*-2 is an empty space, and the front of cover plate main element 14*b*-1 is exposed to the exterior of the apparatus (therefore, when the apparatus is placed in a cooling reservoir, it is exposed to the cooling liquid).

Figure 9:
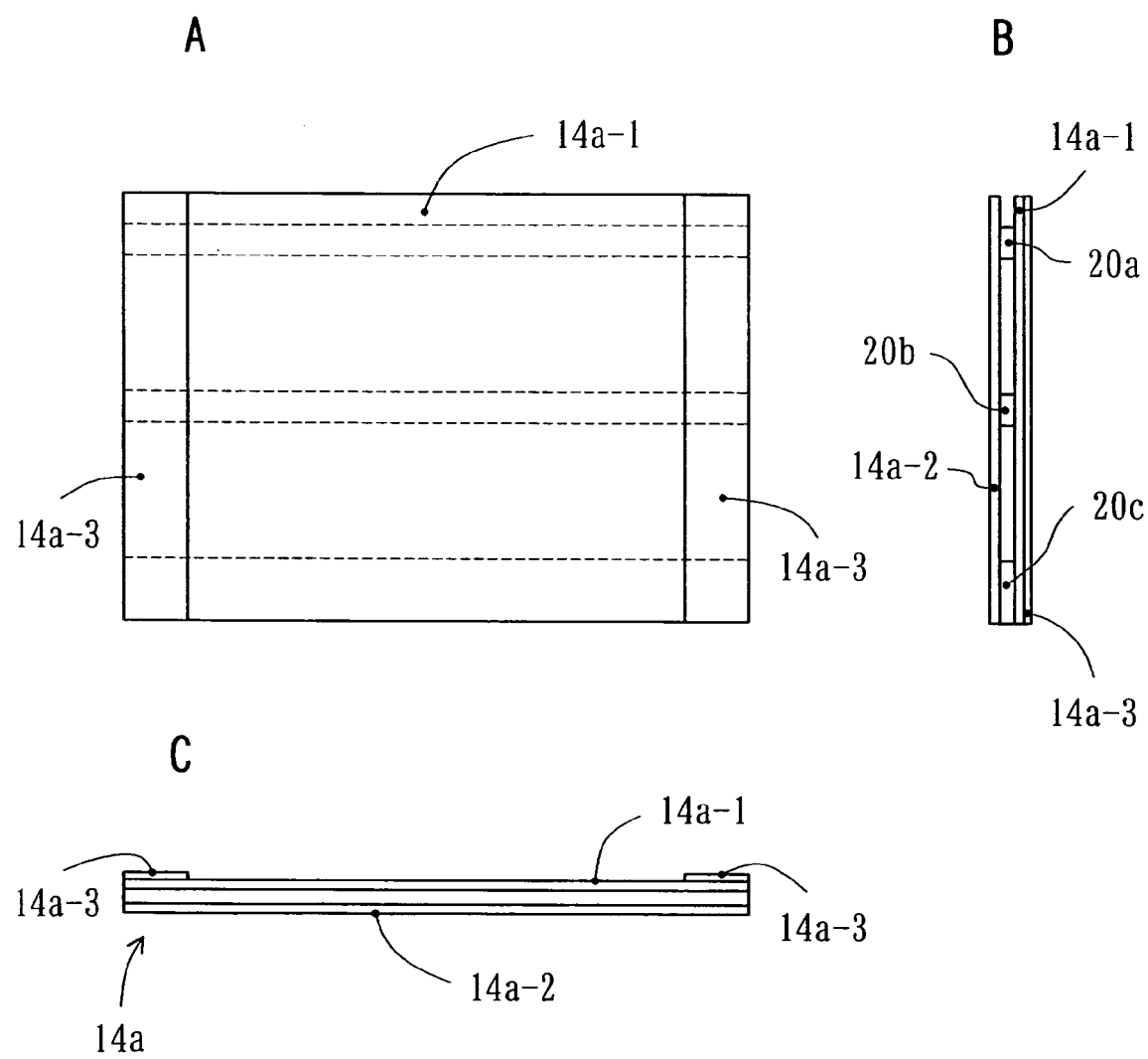
FIG. 9 is a plan view A, right side view B and a view C from the lower end of a gel container plate which is the central element of the second dimension gel container.

FIG. 9 is a plan view A, a right side view B (front side of FIG. 6), and a view from the lower end (C) of gel container plate 14*a* which is the central element of second dimension gel container 2. Container 14*a* comprises a front plate 14*a*-1, which contributes to the formation and maintenance of the gel, and a back plate 14*a*-2. Back plate 14*a*-2 is supported opposite front plate 14*a*-1 on the back side via top, middle, bottom spacers 20*a*, 20*b*, 20*c*. On both sides of the surface of front plate 14*a*-1, gel guides 14*a*-3 are attached, or they are formed as a unit. Therefore, the square flat gel in the second dimension electrophoresis device is formed within the flat space between front plate 14*a*-1 of container plate 14*a* and cover plate 14b (or if there is another gel container 14a, the outer surface of back plate 14a-2 of that gel container plate 14a), corresponding to the thickness of gel guides 14a-3. The extent of the gel is restricted on both sides by gel guides 14a-3. The upper and lower ends of the gel are in contact with the buffer liquid phase in upper buffer reservoir 4 and lower buffer reservoir 1.

Figure 10:
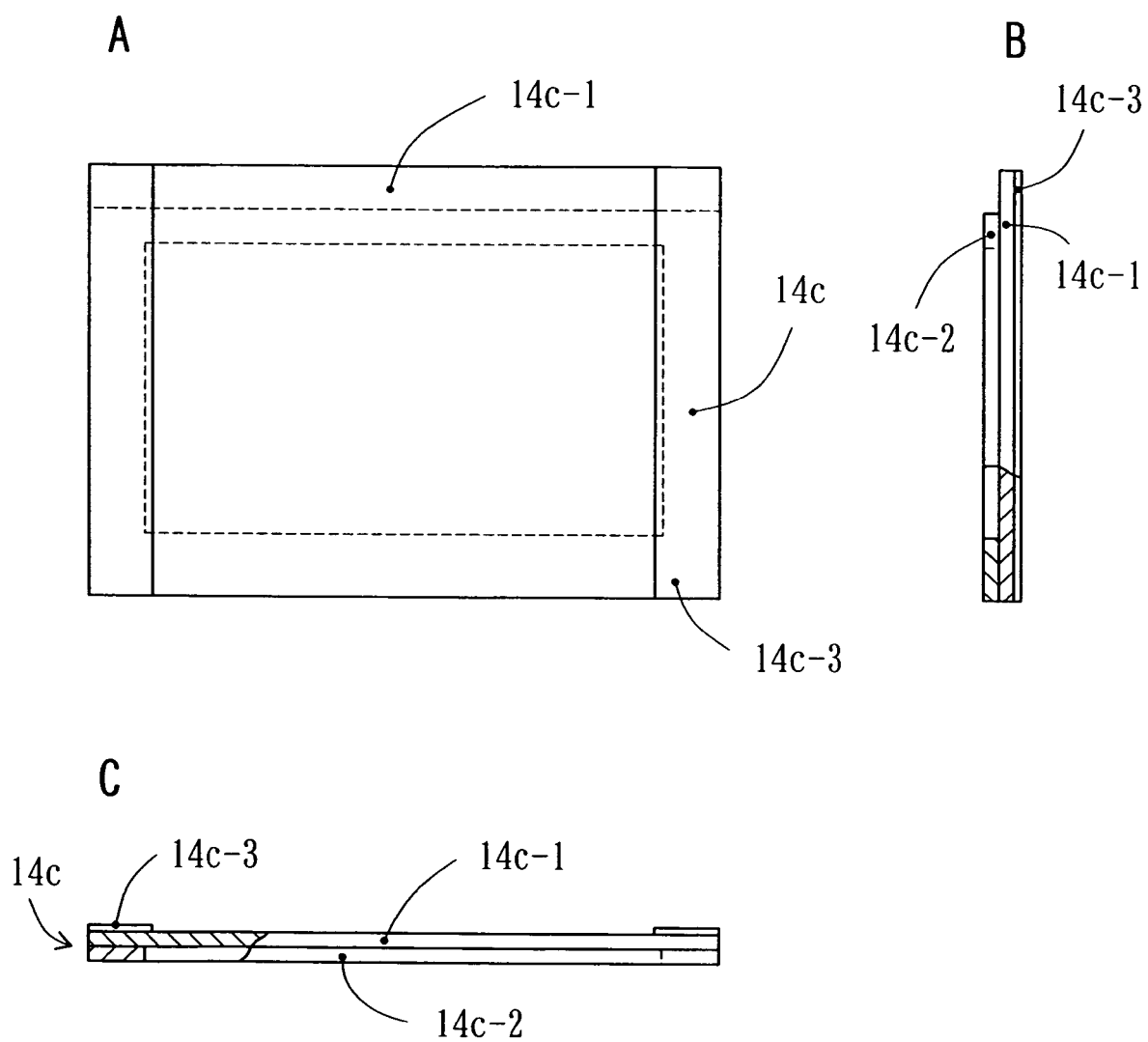
FIG. 10 is a plan view A, right side view B and a view C from the lower end of a container end plate.

FIG. 10 is a plan view A, a left side view B (front side in FIG. 6), and a view from the lower end (C) of container end plate 14c. Container end plate 14c comprises a front plate 14c-1, which contributes to gel formation and maintenance, and a back plate 14c-2, which is supported opposite the back side of front plate 14c-1. On both sides of the surface of front plate 14c-1, gel guides 14c-3, which are similar to gel guides 14a-3 of gel container 14a, are attached, or they are formed as a unit onto front plate 14c-1. Therefore, the square flat gel in the final row (left end of FIG. 6) in the second dimension electrophoresis device is formed within the flat space between back plate 14a-2 of the final gel container plate 14a and front plate 14c-1 of container end plate 14c, with a thickness corresponding to the thickness of gel guides 14c-3. The extent of the gel is restricted on both sides by gel guides 14c-3. The upper and lower ends of the gel are in contact with the buffer liquid phase in upper buffer reservoir 4 and lower buffer reservoir 1. Back plate 14c-2 is a similar frame plate as cover frame plate 14b-2. The inside of the frame is similarly empty space, and it forms a hollow with front plate 14c-1 as the bottom surface.

Figure 11:
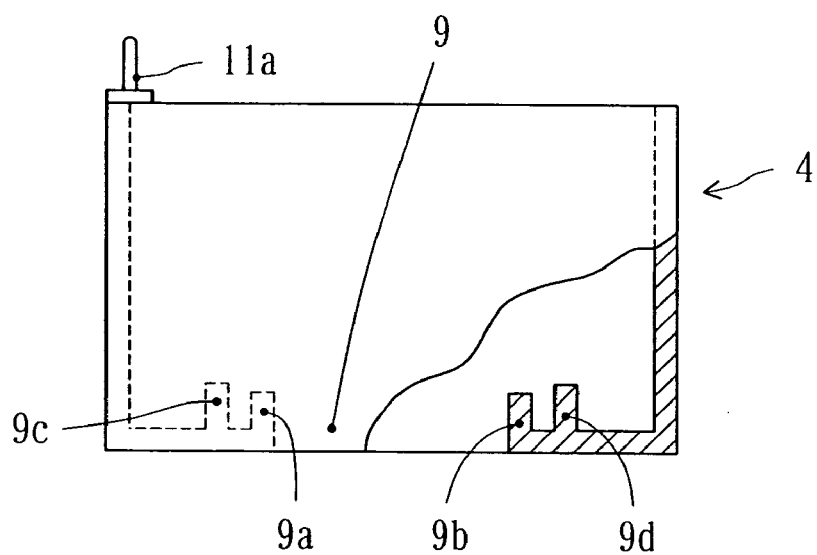
FIG. 11 is a side view A and a plan view B of an upper reservoir of the second dimension electrophoresis apparatus of FIG. 6.
Figure 11:
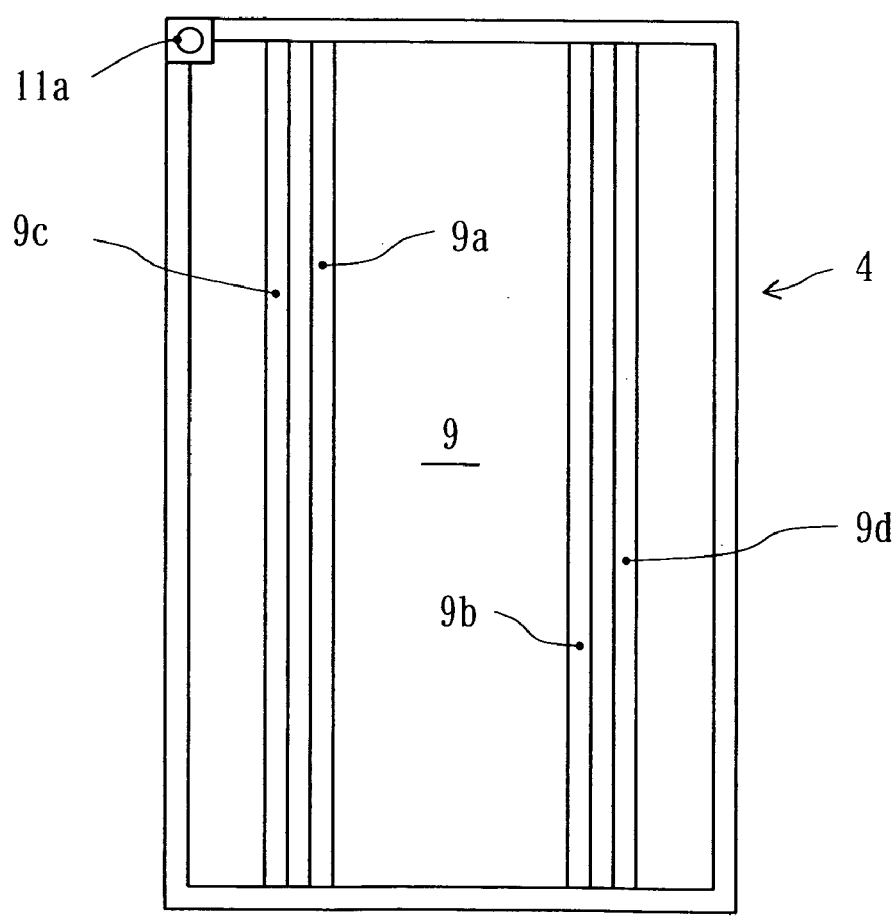

FIG. 11 is a side view A and a plan view B of second dimension upper buffer reservoir 4. Container insertion opening 9, which is in the middle of buffer reservoir 4, is formed between a pair of panel walls 9a, 9b which face each other at a constant distance on the bottom surface in the middle of buffer reservoir 4. Panel walls 9a, 9b have a suitable height, and they are in contact with the upper end of gel container 2 within the range of this height. As a result, the uppermost position of the first dimension electrophoresis apparatus is supported stably. In addition, stopper walls 9c, 9d are formed slightly to the outside of panel walls 9a, 9b on the bottom surface of buffer reservoir 4. Stopper walls 9c, 9d are slightly taller than panel walls 9a, 9b. As will be described later, they play a role in helping gel container 2 stably hold buffer reservoir 4. In addition, an electrode terminal 11a for upper buffer reservoir 4 is attached to the upper end of the corner portion of the side wall and end wall of upper buffer reservoir 4.

The second dimension electrophoresis apparatus assembled as described above is placed inside cooling reservoir 5 as shown in FIG. 6. In the middle area of second dimension gel container 2, the cooling liquid enters inside the space formed between the back surface of front plate 14a-1 and back plate 14a-2 via spacers 20a, 20b, 20c. By cooling the opposing surfaces, the electrophoresis gels are effectively cooled through their thin plates. With cover plate 14b, by cooling the thin cover plate main element 14b-1 which is exposed through the frame opening of cover frame plate 14b-2, the electrophoresis gel is effectively cooled. Back plate 14c-2 is also a frame plate similar to cover frame plate 14b-2, and the thin main element plate of container end plate 14c is also directly cooled. As a result, the left end of the electrophoresis gel is also effectively cooled. The whole apparatus can be effectively cooled together with the upper and the lower buffer liquid and the effect of joule heating which accompanies to the electrophoresis can be near-completely avoided.

In constructing the electrophoresis apparatus in FIG. 6 recited above, as in the apparatus in FIG. 1, the lower end of the gel container 2 is placed into the gel container insertion opening 6 of the lower buffer reservoir 1 and then, a seal agent S is filled into the crossing parts between them and the seal agent S is air-dried and the crossing part is glued and sealed. The crossing part between the upper end of the gel container 2 and the container insertion opening 9 of the upper buffer reservoir 4 is glued and sealed in the same way. After completion of sealing, a liquid gel is poured into the gel chamber 3 and it is left for a few minutes to be a gel. As a result, a gel plate is made in the gel chamber. A pre-prepared gel may be packaged into the gel chamber 3 in the gel container 2 in the apparatus of this invention wherein the crossing parts of the gel container and both gel container insertion openings have been previously glued and sealed.

Figure 12:
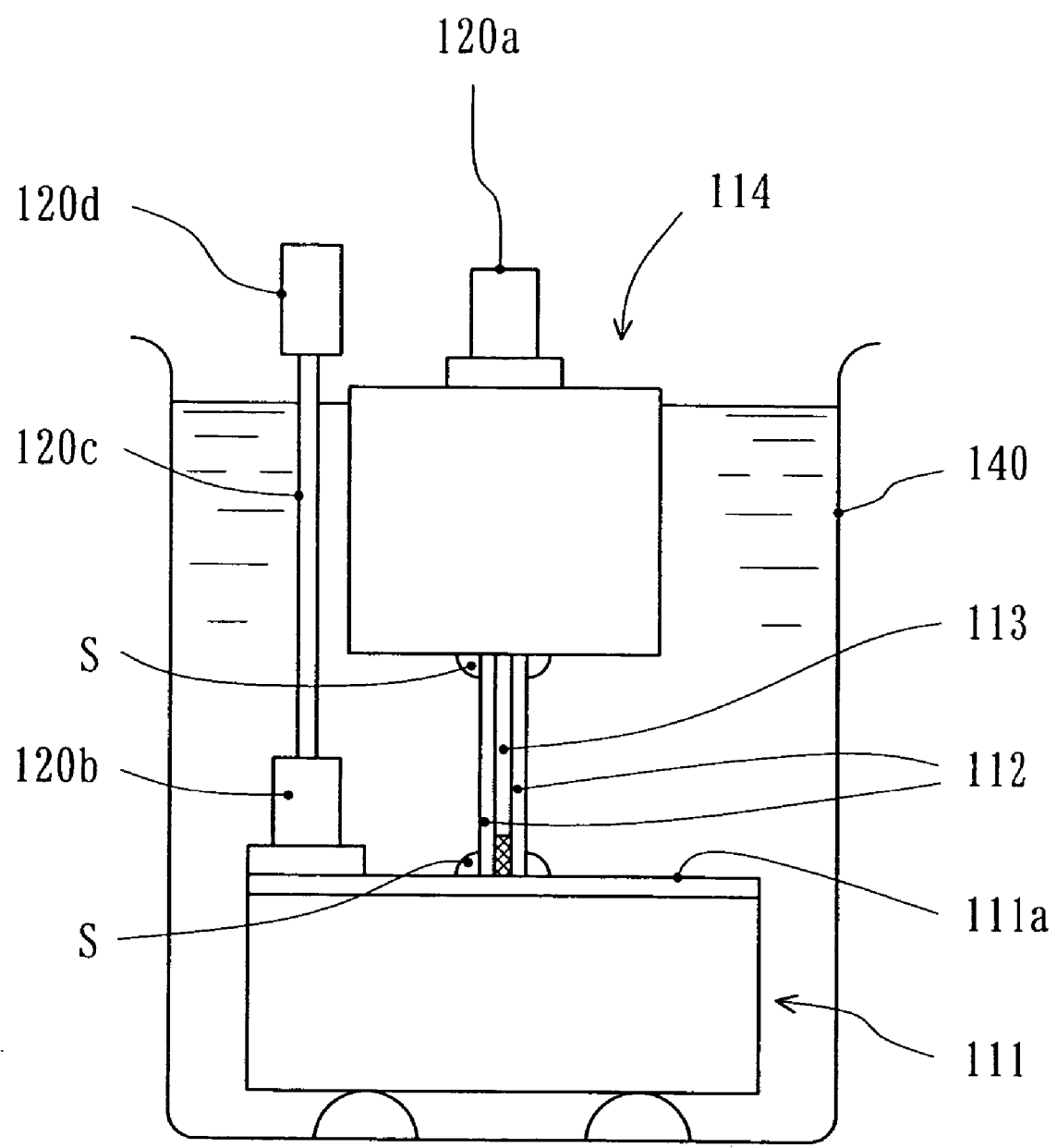
FIG. 12 is a schematic drawing of another example (a vertical type) of a first dimension electrophoresis apparatus of this invention.

FIG. 12 is a schematic drawing showing a different embodiment of a first dimension electrophoresis apparatus of this invention. There is a lower buffer reservoir 111, a gel container 112 in which a plurality of upright, rod-shaped gel chambers 113 are arranged in parallel, and an upper buffer reservoir 114. These are all formed from plastic which is corrosion-resistant and which has excellent electrical insulation and mechanical strength. Lower buffer reservoir 111 has an upper cover 111a, which connects with the lower end opening of gel chamber 113 and supports gel container 112 in a liquid tight condition. Lower buffer reservoir 111 has an insulated electrode terminal 120b for the lower buffer reservoir electrode (not shown) which hangs from upper cover 111a. From electrode terminal 120b, a conductive column 120c, which has an insulation covering, stands upright to a height that is greater than the height of the opening for cooling reservoir 140. The upper end of conductive column 120c is equipped with a lower buffer reservoir electrode terminal 120d. Terminal 120b, conductive column 120c, and buffer reservoir electrode terminal 120d have a narrow direct communication space in order to allow gas which is generated in the lower buffer reservoir to escape. The upper end of upper buffer reservoir 114 is at least the same height or greater as the opening for cooling reservoir 140. Upper buffer reservoir 114 has an electrode terminal 120a which protrudes upward from the upper cover or (in case there is no upper cover) from the inner side wall. As a result, except for the upper end of upper buffer reservoir 114 and electrode terminals 120d and 120a, essentially the entire apparatus can be submerged in a cooling liquid within a cooling reservoir 140. In this example, too, the crossing part between the upper cover 111a on the lower buffer reservoir and the gel container 112 and the crossing part between the upper buffer reservoir 114 and the gel container 112 are completely liquid tightly sealed with, for example, a sealing agent, to prevent invasion of cooling liquid into the gel chamber when the apparatus is sunk in the cooling reservoir.

Figure 13:
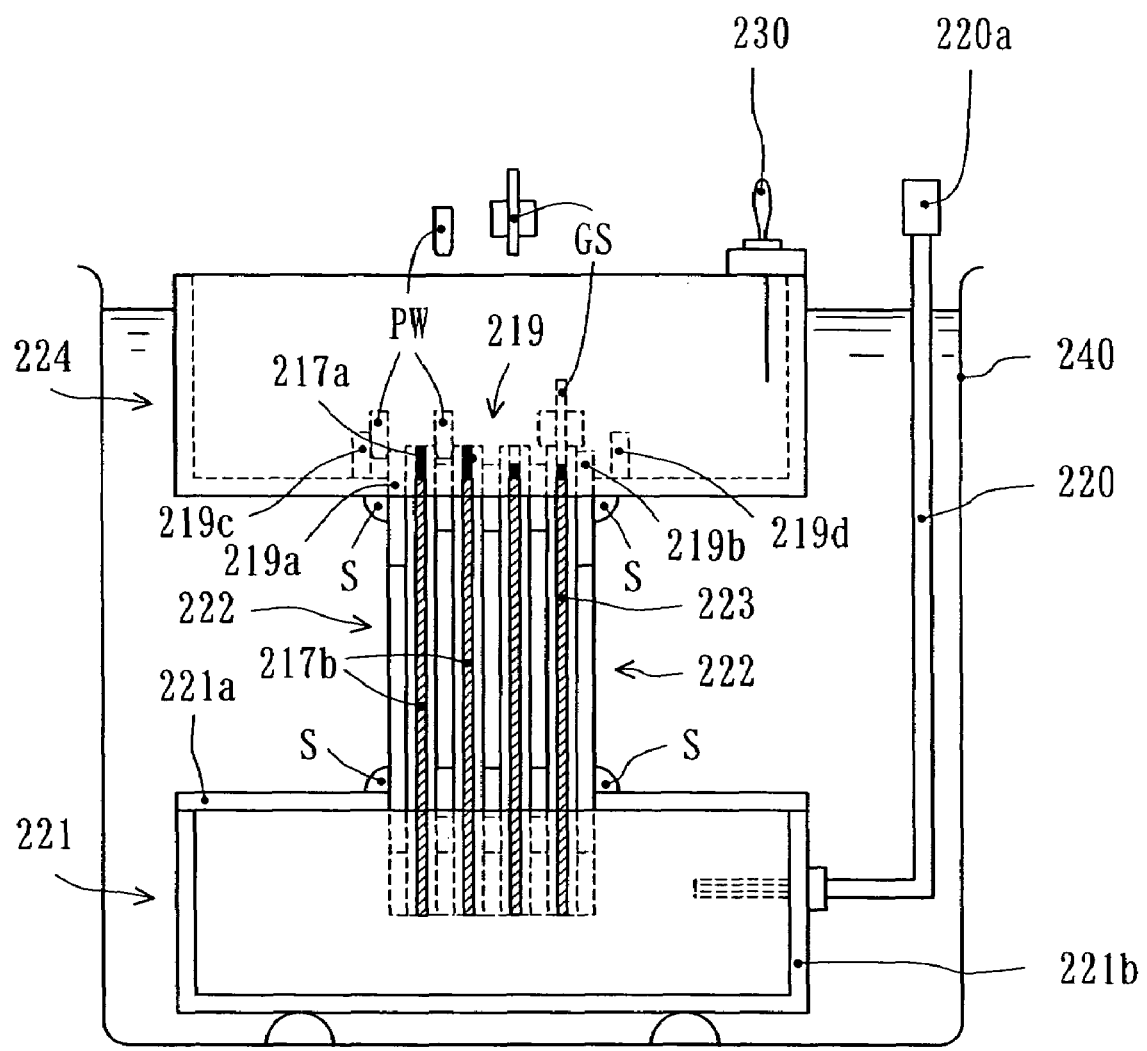
FIG. 13 is a schematic drawing of another example (a vertical type) of a second dimension electrophoresis apparatus of this invention.

FIG. 13 is a cross-section showing another embodiment of a second dimension electrophoresis apparatus in which electrophoresis is conducted after placing a first dimension gel is on top of a second dimension gel. There is a lower buffer reservoir 221, a gel container 222, in which a plurality of flat gel chambers 223 are placed upright in an overlapping and parallel condition, and an upper buffer reservoir 224. These are all formed from corrosion resistant plastic with excellent electrical insulation and mechanical strength. Lower buffer reservoir 221 has an upper cover 221a, which connects with the lower end opening of gel chamber 223 and supports gel container 222 in a liquid tight condition. Lower buffer reservoir 221 has a pipe 220 covered with insulation, for leading out the leading wire which connects to an internal electrode. As shown in the figure, the pipe 220 is bent upward from side wall 221b. Terminal 220a at the upper end of the pipe 220 protrudes from the upper level of cooling liquid in the cooling reservoir 240. The pipe 220 and buffer reservoir electrode 220a have a narrow direct communication space in order to allow gas which is generated in the lower buffer reservoir to escape. As a result, except for the upper end of upper buffer reservoir 224 and terminals 220a and 230, essentially the entire apparatus can be submerged in a cooling liquid within a cooling reservoir.

On the bottom surface of upper buffer reservoir 224, there are panel walls which form the side walls for gel container insertion opening 219. Slightly to the outside of the panel walls 219a, 219b, plug walls 219c, 219d, which are slightly taller than the panel walls, are formed. Panel walls 219a, 219b, and the plug walls 219c, 219d have the same relationship as the panel walls 9a, 9b and plug walls 9c, 9d in FIG. 11. The panel and plug walls 9a-9d in FIGS. 11 and 219a-219d in FIG. 13 have an effect recited above of serving for stably supporting of the buffer reservoir by the gel container. They also have the following effect. That is, after inserting the upper end of gel container 222 (2 in FIG. 6) into insertion opening 219 (9 in FIG. 6 and FIG. 11), a gauze (which is not shown in Figure) is placed on side walls (panel walls), of insertion opening 219(9) and plug walls 219a(9a), 219b(9b), and the upper end of gel container 222(2). By inserting plug PW and gasket GS, gauze is held in place. As a result, upper buffer reservoir 224(4) and gel container 222(2) are fastened, and the first dimension gel(217a, 7a) are tightly placed on the second dimension gel(217b, 7b) in the gel chamber without aparting from the top of the second dimension gel into the upper gel buffer.

Figure 4:
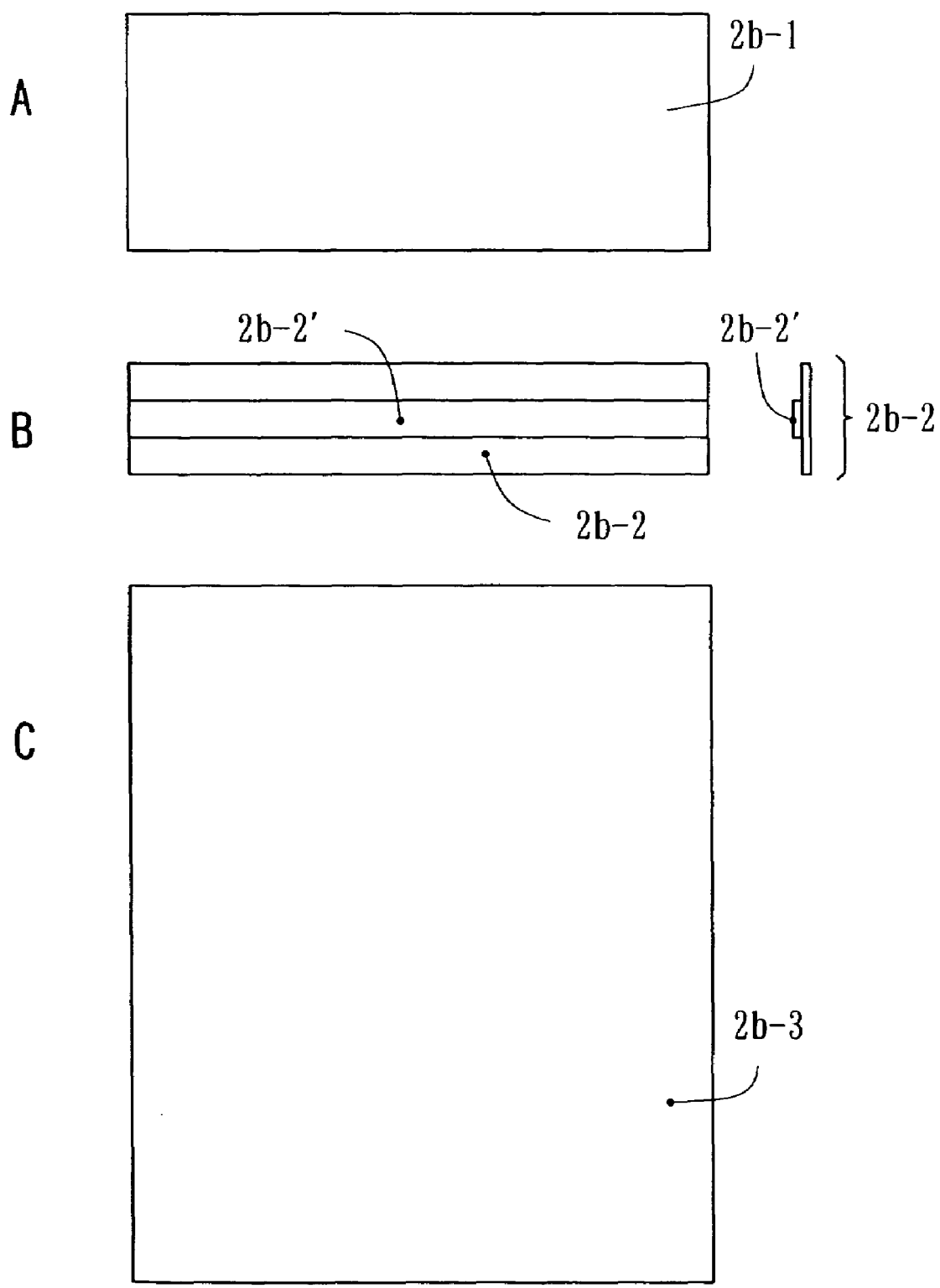
FIG. 4 is a front view A of the top cover plate of the gel container and a front view B of a window cover plate and front view C of a lower cover plate of the first dimension electrophoresis apparatus of FIG. 1.
Figure 14:
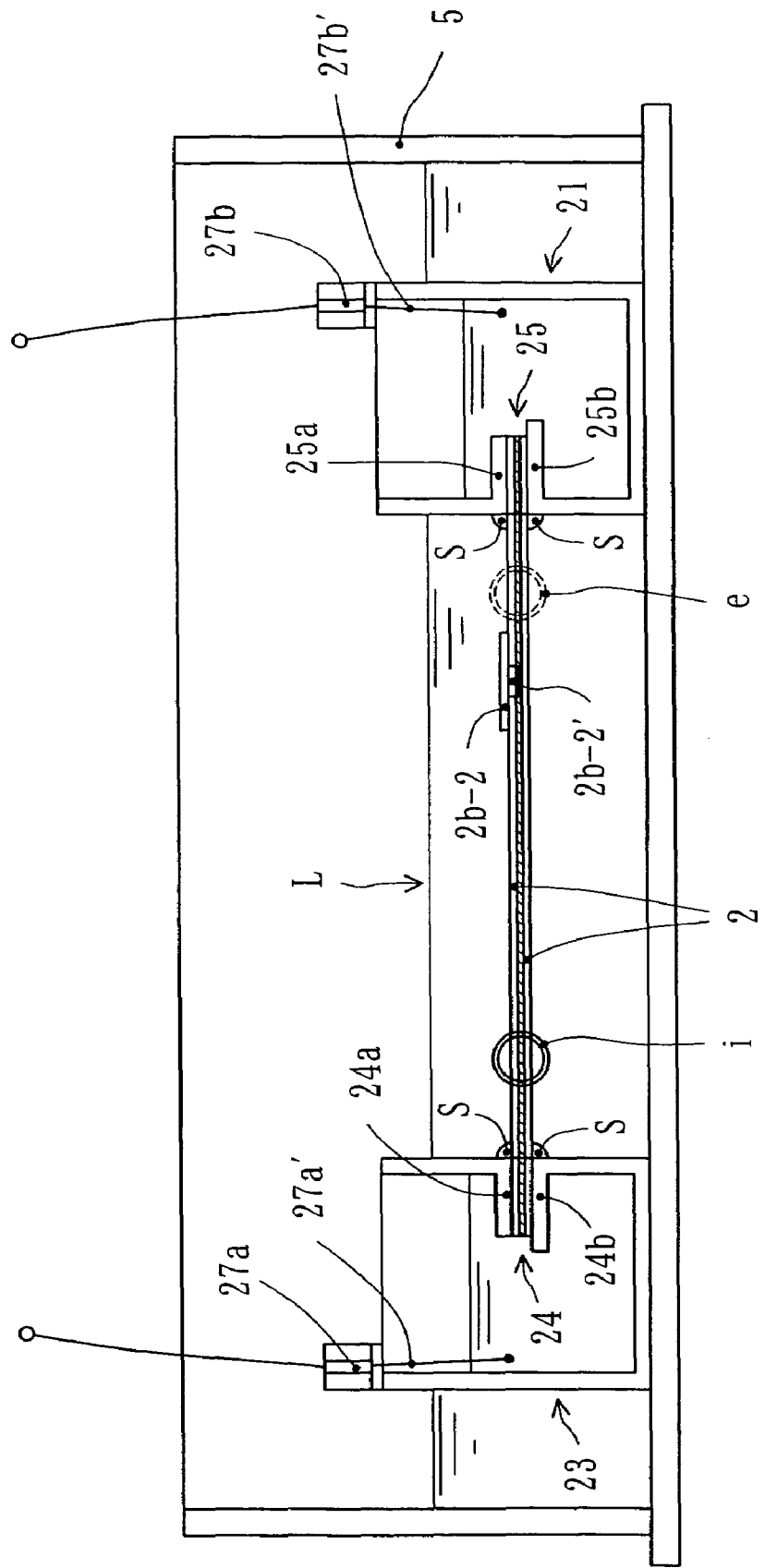
FIG. 14 is a schematic drawing of an example (a horizontal type) of a second dimension electrophoresis apparatus of this invention.

FIG. 14 is the fifth example (a horizontal type) of a first dimension electrophoresis apparatus of this invention, wherein the gel container is placed horizontally. 21 is the first buffer reservoir, 23 is the second buffer reservoir, and a downstream part gel buffer reservoir, 2 is a gel container in which a plurality of rectangular rod-shaped gel chambers are horizontally arranged in parallel The gel container 2 has a same window cover plate 2b-2 and a same window cap 2b-2' as in the apparatus in FIG. 1 in the position near upstream in the gel container 2 and has a same structure as the gel container 2 in FIG. 4. In practicing electrophoresis, the sample at the middle part in the gel container 2 flows from the upstream portion (an open end of the gel container 2 into the first buffer reservoir 21) to the downstream portion (a open end of the gel container 2 into the second reservoir 23). An electrode terminal 27a of the second buffer reservoir 23 is attached to the upper end of the second buffer reservoir 23. 27a is connected to a platinum wire 27a' which is immersed in the buffer solution inside the second buffer reservoir 23. With platinum wire 27a', the lower end, which is hanging approximately 20 mm from the upper end of the buffer reservoir, is bent so that it is horizontal and is spread along the entire length of the panel portion. An electrode terminal 27b and 27b' of the first buffer reservoir 21 is attached to the upper end of the first buffer reservoir 21. In the FIG. 14, L is a surface of cooling liquid. The cooling reservoir has an opening i for pouring cooling liquid and an opening e for discharging cooling liquid in the same way as in the reservoirs in FIG. 1 and FIG. 6. The container insertions 24 and 25 are sealed with a sealing agent S in the same way as in the electrophoresis apparatuses in FIG. 1 and FIG. 6.

Figure 15:
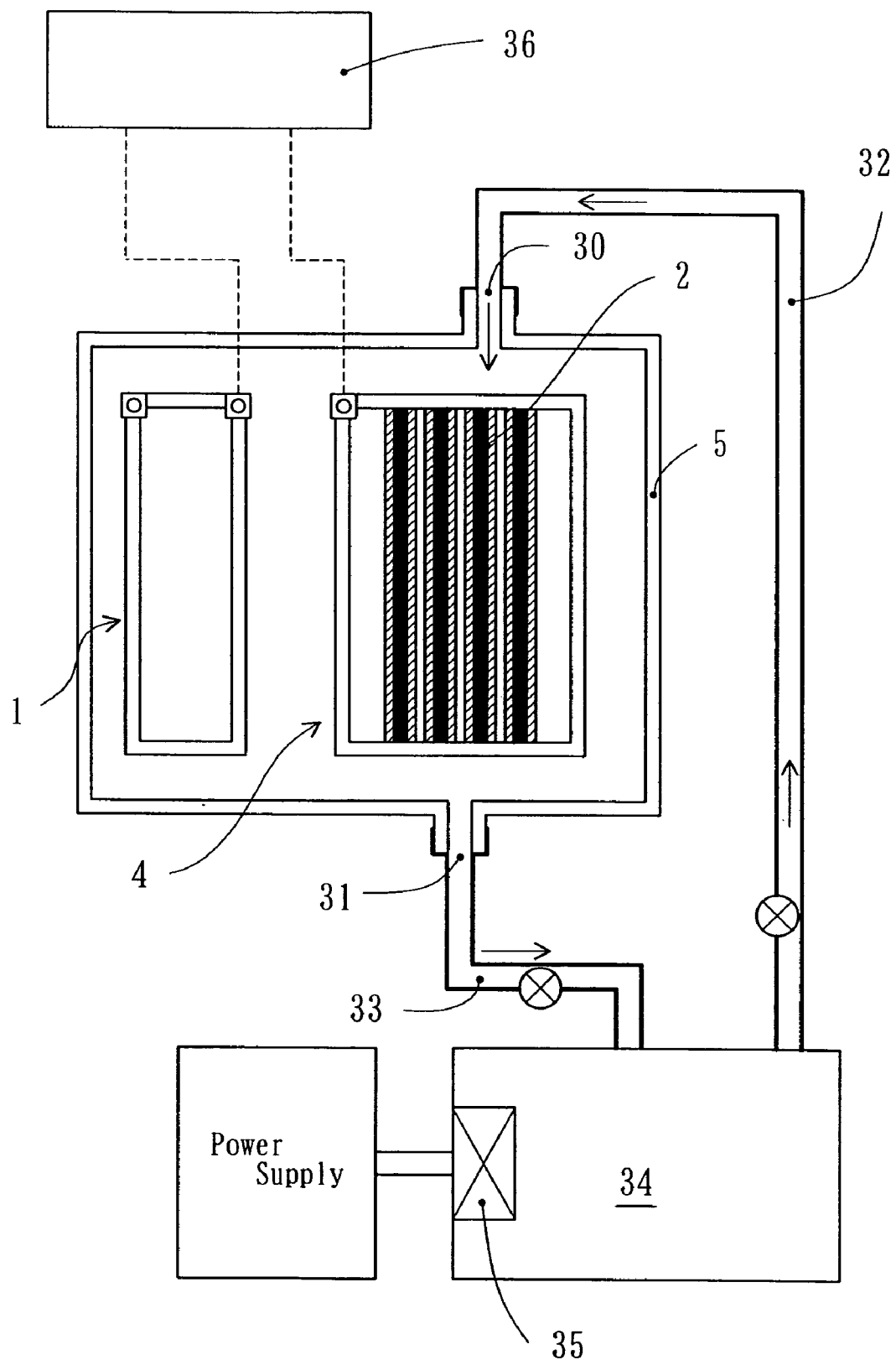
FIG. 15 is a plan view which shows the preferable arrangement of a gel container, an opening for pouring cooling liquid on the side of the cooling reservoir, an opening for discharging cooling liquid on the opposite side of the cooling reservoir, and other accompanying devices, when the whole electrophoresis apparatus of this invention (in FIG. 6) has sunk in a cooling reservoir.

FIG. 15 is a plan view which shows the preferable arrangement of a gel container, an opening for pouring cooling liquid on the side of the cooling reservoir, an opening for discharging cooling liquid, and other accompanying devices, when the second dimension electrophoresis apparatus of this invention in FIG. 6 is sunk in the cooling reservoir. The opening 30 for pouring cooling liquid is positioned near the center of one side wall of the cooling reservoir 5. The opening 31 for discharging cooling liquid is positioned near the center of opposite side wall against to the side wall which the opening 30 is positioned. As recited above, the electrophoresis apparatus should preferably be sunk and positioned in the cooling reservoir 5 in such a way that the middle portions of respective sides of the gel container 2 of this invention face to the opening 30 and 31 respectively in order to cool the gel most effectively. In this figure, the numerals 1, 2 and 4 correspond to those in FIG. 6. The openings 30 and 31 are connected respectively with pipes through to a tank 34 for cooling liquid. In the tank 34, there is a temperature controller 35 whereby cooling liquid is maintained at temperature range of 4-10° C. 36 is an electric power source for supplying electrophoresis voltage and temperature controller.

Figure 16:
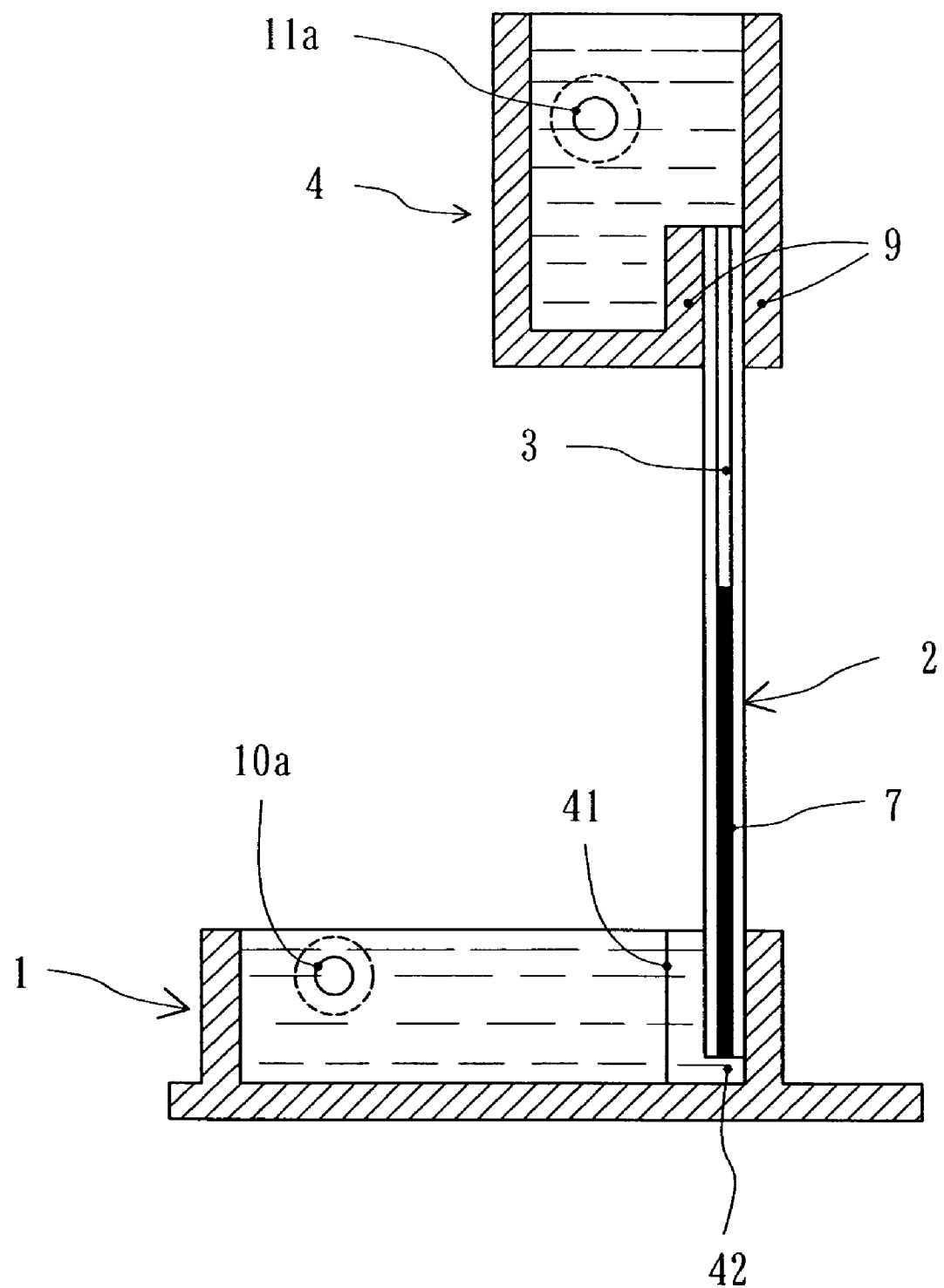
FIG. 16 is a lateral cross-section showing a zero dimension electrophoresis apparatus assembled for zero dimension electrophoresis.

FIG. 16 is an example showing zero dimension electrophoresis apparatus which is used for a pre-treatment in implementing the electrophoresis method when the more accurate electrophoresis assay results are required. 1 is a lower buffer reservoir, 2 is a gel container in which a plurality of rod-shaped gel chambers 3 are vertically arranged in parallel, 4 is a upper buffer reservoir, which are formed from plastic or glass which is corrosion-resistant and which has excellent electrical insulation and mechanical strength.

The lower end of gel container 2, which has a lower end opening for gel chamber 3, is inserted so that it forms a bridge between the inside of corner partitions 41 of lower buffer reservoir 1 and the back wall. By having the lower end of gel container 2 placed on top of support platforms 42 between partition pieces 41 and the back wall, a space of the height of support stage 42 is created between the lower end of gel container 2 and the lower surface of the reservoir along most of the length of the gel container except for the length of partition pieces 41 on either side. The lower end of gel 7, which fills the lower part of the inside of the gel chamber, is in contact with buffer solution. In addition, the upper part of gel container 2 is inserted and affixed to container insertion opening 9 in the back part of upper buffer reservoir 4. The upper end opening of gel chamber 3 is in communication with the liquid phase inside upper buffer reservoir 4. Electrode terminals 11a, 10a are electrical conductors attached to upper buffer reservoir 4 and lower buffer reservoir 1, respectively.

(The Best Mode for Implementing the Invention)

The experiments explained precisely as follows are those regarding to assays of proteins by the methods of this invention, wherein the apparatuses of this invention in FIG. 1-16 were used. In these experiments, the RFHR method as a pretreatment was used for concentrating the sample.

Experiment 1

Prior to first dimension electrophoresis, electrophoresis was conducted at a pH 5.5 in a pre-treatment bar-shaped gel through a potassium acetate buffer solution containing 7M urea with K+ as the leading ion and glycine and cysteine as the trailing ions. Protein of pH 4.0 or greater with a variety of isoelectric points were concentrated towards the negative electrode.

First dimension electrophoresis was conducted by placing the zero dimension gel segment obtained in this manner on top of the upper end of the first dimension gel material. For the basic region, the entire length of the rod-shaped first dimension gel was set at a pH 8.6, and the electrode on the upper buffer reservoir was used as an anode, and the electrode of the lower buffer reservoir was used as the cathode. In addition, for the neutral to acidic region, the pH was set at 9.8, and the electrode on the upper buffer reservoir was used as a cathode, and the electrode on the lower buffer reservoir was used as an anode. The proteins migrate at a constant speed with their net charge as the driving force, and the proteins separate due to differences in their speeds. The gel buffer was a tris boric acid buffer containing 7 M urea and 0.32% EDTA-2 sodium.

Second dimension electrophoresis was conducted by placing the first dimension gel, obtained as described above, on the upper end of the second dimension gel material. A potassium acetate buffer solution containing 7M urea was used. The entire gel was set at a constant pH of 3.4. With this pH, all proteins migrate downward toward the cathode of the lower buffer reservoir. The gel (polyacrylamide gel) concentration for the zero-dimension and first dimension migration was 7%. The gel concentration for the second dimension migration was 16%. However, depending on the size of the protein molecule, the gel concentrations can be changed as suitable. The second dimension gel has a size of thickness of 2 mm, width of 165 mm, and height of 135 mm. With the apparatus construction described above, four gels of this size can be used simultaneously. In addition, in order to eliminate free radicals remaining in the gel, prior to insertion of the sample gel piece, a pre-run of mercaptoethylamine hydrochloride as a radical capture agent was conducted on the anode side.

Next, the creation and addition of sample gel was explained. Normally, freeze-dried protein sample that has been demineralized was dissolved in 1.4% 2-mercaptoethanol and 8M urea, and this was pre-incubated for 30 minutes at 40 degrees C. Next, a 1/50 amount of a 50 times solution of zero dimension gel buffer containing pyronine Y and acridine orange as front markers was added. The concentration was 2-4 mg/ 0.1 mL, and a few mg per gel can be added.

Zero dimension electrophoresis operation: After completing the pre-run, sample solution was placed on the zero-dimension gel. For the electrode solutions, a glycine acid buffer containing 4 M urea and 3.5% cysteine hydrochloride was used for the anode, and the zero-dimension gel buffer was used for the cathode. Under room temperature, electrophoresis was conducted for approximately 15 minutes with a constant voltage of 100V. As the sample gel, the top 10 mm of the gel which includes the pyronine Y and acridine orange band was cut out, and this was inserted into the first dimension gel.

First dimension electrophoresis operation: The window provided in the middle of the first dimension gel was opened. Approximately 10 mm of the first dimension gel was cut and removed, and in its place, the sample gel of the same length was inserted. The electrode solution was the same as the first dimension gel buffer, and on the anode side, as a reducing agent, 0.5% metcaptoethylamine hydrochloride was added, and electrophoresis was conducted. The temperature was 4 degrees C., and the voltage was a constant 500V. For the basic region, electrophoresis was conducted for 6 hours, and for neutral to acidic region, electrophoresis was conducted for 20 hours.

Second dimension electrophoresis operation: The first dimension gel was laid on top of the second dimension gel. For the electrode solution, a glycine buffer containing 4 M urea and 3.5% cysteine hydrochloride was used at the anode. At the cathode, the same buffer as for the anode was used, except cysteine hydrochloride was not included. Electrophoresis was conducted at 4 degrees C. with a constant voltage of 300 V for 12 hours for the basic region and for 30 hours for expanding the neutral to acidic region. In all dimensions, the reducing agent migrates at the same time as the protein molecules, and a highly reducing environment is maintained.

In the RFHR two dimensional electrophoresis method implemented as described above, in order to conduct even further detailed analysis, an expanded two dimensional image was created simply by extending the migration time in both the first and second dimension operations. For example, for expanding the neutral to acidic region, the first dimension operation was made to be 40 hours, and the second dimension operation was 60 hours.

Dyeing and bleaching: In general, Coomasie brilliant blue (CBB) dyeing was conducted. Dyeing was conducted with 1.25% CBB G200, 45% methanol, and 9% acetic acid. Bleaching was conducted once with 25% methanol and 7.5% acetic acid, and subsequently a process of bleaching with 2% acetic acid was repeated. If necessary, silver dye, fluorescent dye, or amido black dye was also used.

Characteristics of the RFHR Method as Seen from the Above Experiments:

(1) Because there is no restriction on the isoelectric point, regardless of the basicity or acidity, the same separation can be performed. In other words, with a immobilized pH gradient method, the range where good separation can be achieved is in the range of pH 10 or less. On the other hand, with the present RFHR method, the separation capability is the same regardless of the isoelectric point. As a result, for proteins with an isoelectric point of pH 10 or greater, there is better separation with the RFHR method. This difference is important in proteome which has a goal of comprehensive protein analysis. With the proteomics of the prior art, because of the weakness of the immobilized pH gradient method, a large portion of base proteins were essentially ignored. With the introduction of RFHR method this is improved, this disadvantage is eliminated.

(2) With RFHR method, one type of protein converges on one spot. In contrast, with the immobilized pH gradient method of the prior art, because a first dimension gel with a narrow pH gradient is used, a protein spot can be analyzed very precisely. But conversely, when first dimension electrophoresis is conducted on each protein, each of the proteins divides into several conformations. Depending on the conformation, different spots are formed. There is artificial splitting of the spots. This is a defect of the immobilized pH gradient method and is unrelated to modifications in the cell. On the other hand, with the RFHR method, this artificial splitting does not occur. The RFHR method has the advantage of having a one to one correspondence between protein and spot. The difference between the two methods can be seen in the different number of genes that can be identified from the spots.

(3) The fact that there is a large amount of protein added per gel is also a reason for the high rate of identification. In other words, the protein gene identification rate is a direct reflection of the amount of protein added to the gel. With the RFHR method, the protein amount is 5-8 mg and is several times that of the immobilized pH gradient method. Therefore, in contrast with the low rate of identification due to the splitting of spots seen in the immobilized pH gradient method, with the RFHR method, the identification rate is almost a factor of 10 higher. Of the spots that can be identified with CBB dye, 80-90% can be identified by mass spectrometry.

(4) Because SDS (sodium dodecyl sulfate salt) is not used in the first dimension, there is a high probability of recovering the structure and function after separation. With the RFHR method, SDS is not used, and only urea is used as the solubilizing agent. Therefore, the driving force for protein migration is the positive net charge of the protein itself in a pH of 3.4. The migration speed is determined by the net charge per molecular weight and the effect of molecular sieving. Even without SDS, the separation capability is not compromised. Conversely, the probability of recovering the function of the separated protein is higher. The protein is only mildly denatured by urea, and by equilibrating the second dimension gel with a suitable buffer, the function can be recovered. It is possible to conduct function measurements for all of the protein distributed on the gel all at once.

Figure 17:
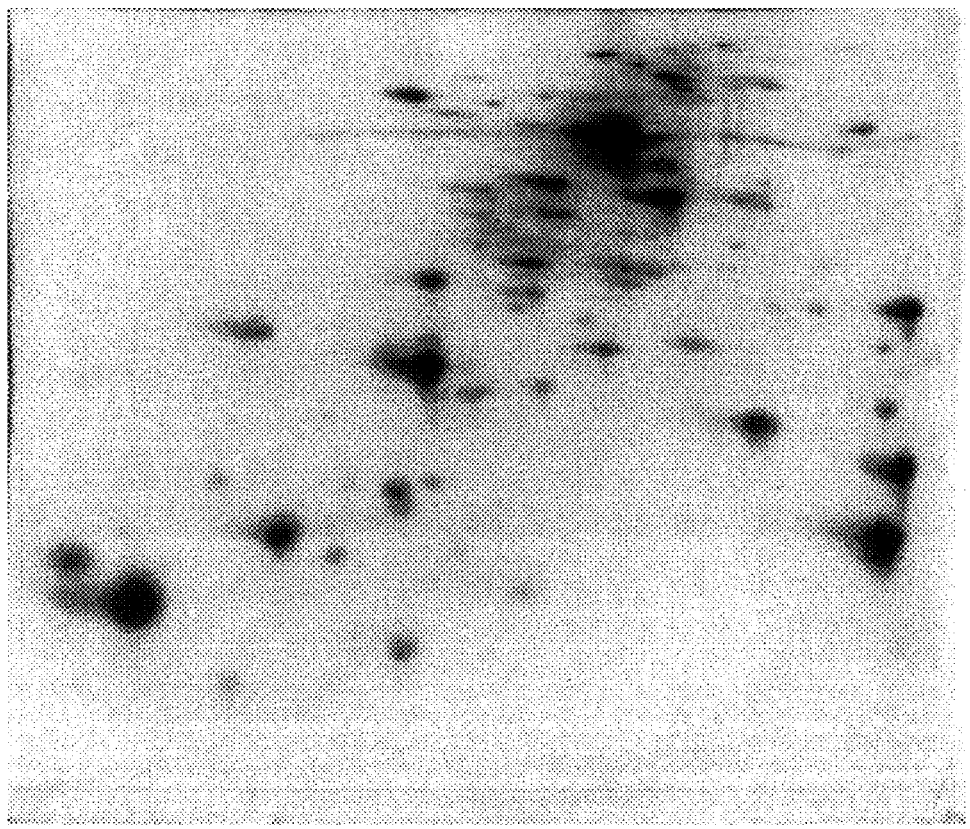
FIG. 17 is an enlarged view of a neutral to weakly acidic region of a CD protein.
Figure 18:
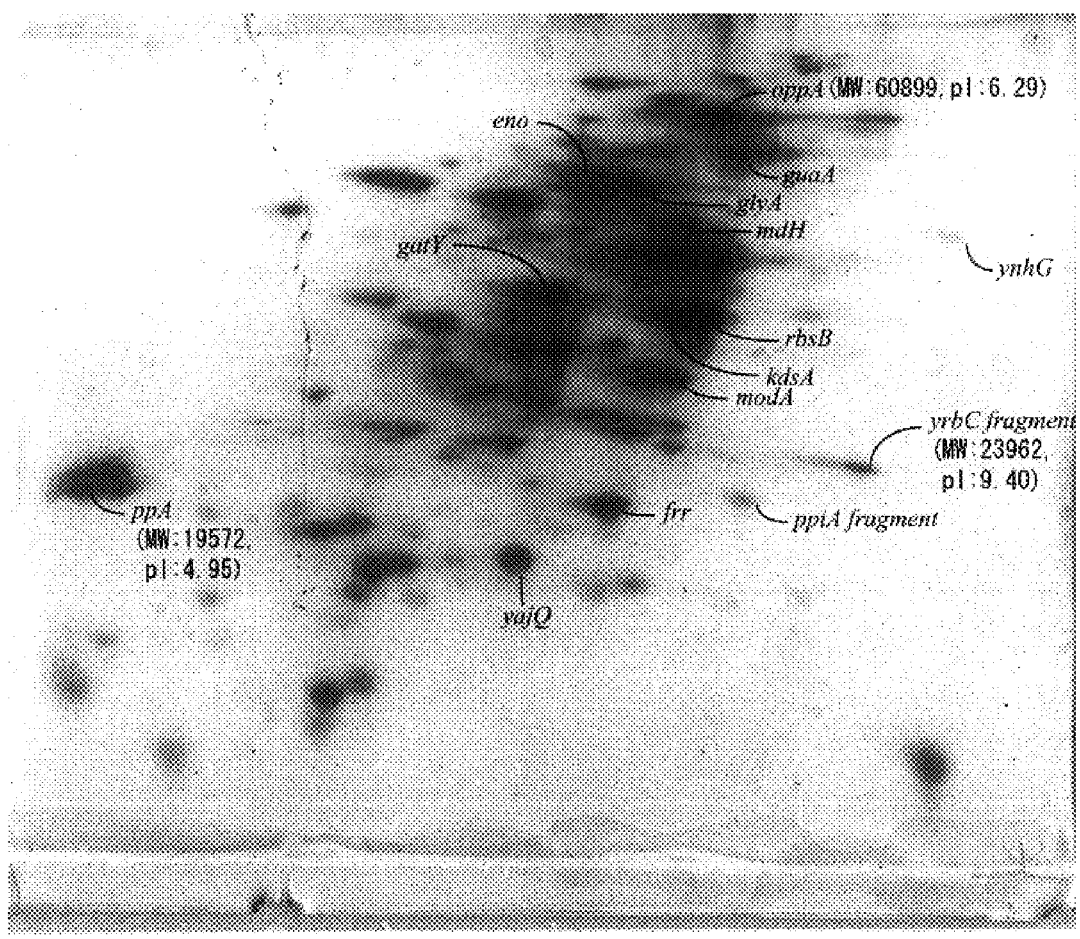
FIG. 18 is an enlarged view of a neutral to weakly acidic region of a PRS protein.

(5) A detailed two dimensional image can be created by extending the migration time. With the immobilized pH gradient method, first dimension gels with different ranges of pH gradient are prepared. Different ones are used depending on the necessary precision. On the other hand, with the RFHR method, by extending the migration time for the second dimension, the two dimensional image is expanded in the horizontal and vertical direction. In particular, proteins, mainly enzyme proteins, are concentrated in the neutral to weakly acidic region. Therefore, by having migration condition that can adequately expand this region, application for proteome becomes possible (FIGS. 17 and 18).

(6) The quantitative quality of protein which returns to a spot is high. On the two dimensional gel of the immobilized pH gradient method, in both the vertical and horizontal directions, there is loss of protein which has ribbon-like dye. In addition to the splitting of spots as described above, the quantitative quality of proteins returning to its original spot is low. With RFHR method, there is no ribbon-like dyeing. In addition, by having a charged reducing agent migrate at the same time, a highly reducing environment is maintained in the gel, and as a result, there is no loss due to SS cross-linking during migration. The high quantitative quality of the RFHR method is confirmed through numerous analyses of ribosomal protein.

Figure 19:
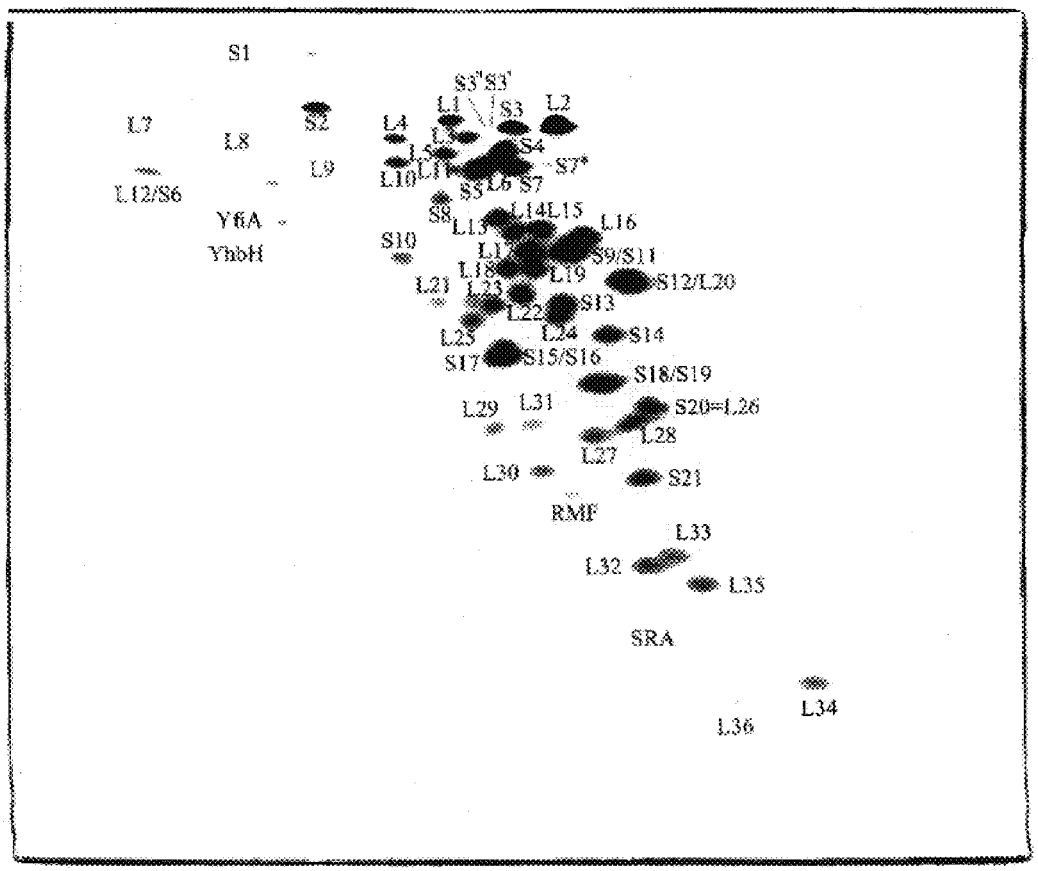
FIG. 19 is a plan view showing a two dimensional gel (L=50S, S=30S ribosomal protein) emphasizing the base region of a CR protein.

Below, we will describe an example where the RFHR method is used for E. coli proteomics. First, bacteria harvested at the steady period was ground. Next, these were divided into an insoluble cell debris fraction (CD), crude ribosomal faction (CR), and soluble fraction other than CR (post-ribosomal supernatant PRS). The proteins in each fraction were analyzed by RFHR method. In the study of the two dimensional gels, the right side was negative (base) and the left side was positive (acidic). Referring to FIG. 19, the proteins in the CR fraction were separated under migration conditions that emphasize the basic region. All of the ribosomal proteins were included here. Of these, L35, L36 and L31 could not be detected by the K-W method which is the original method for RFHR method. These were ribosomal proteins discovered for the first time with the RFHR method. With this discovery, E. coli ribosomal proteins have been completely defined.

Figure 20:
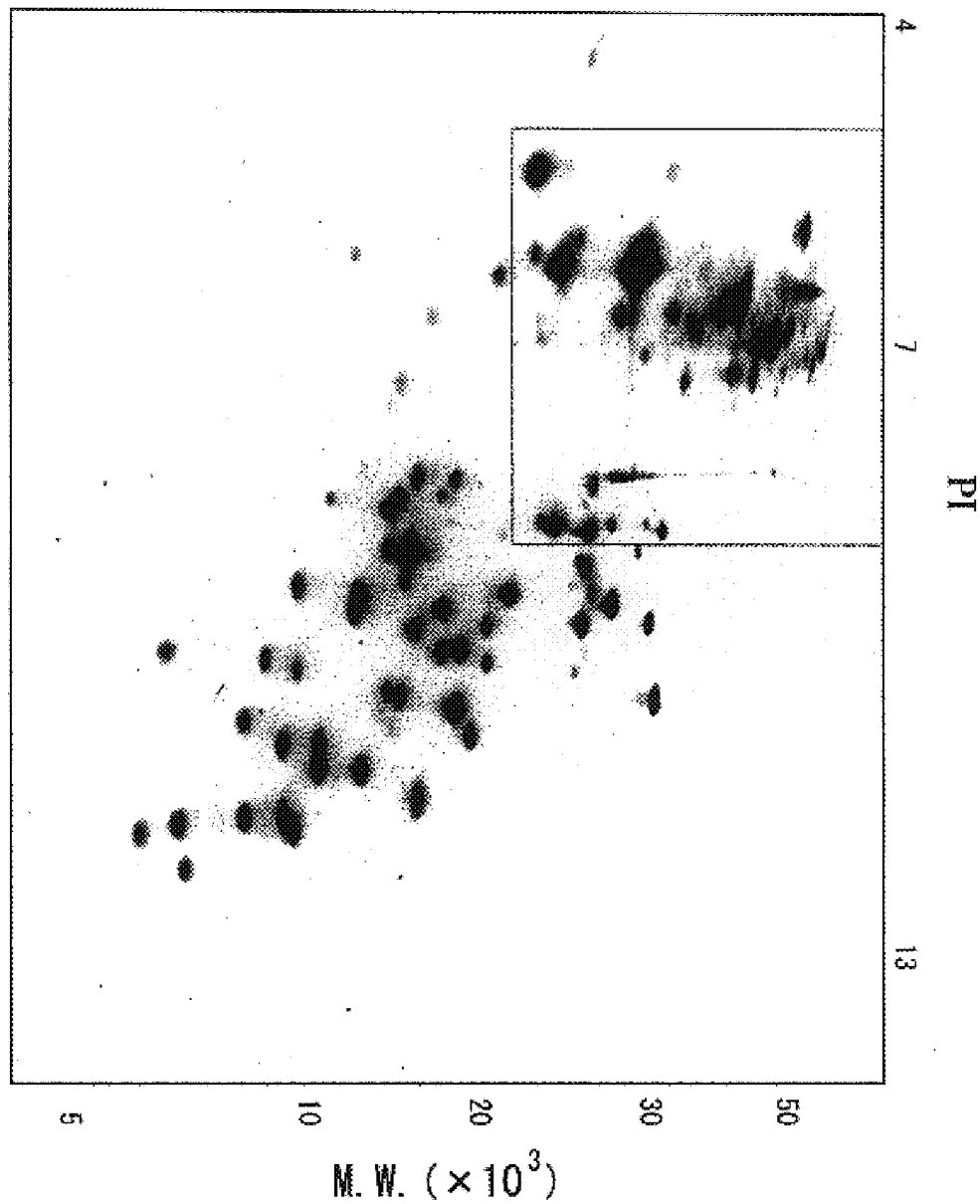
FIG. 20 is a plan view of the two dimensional gel emphasizing the base region of the CD protein, and the enclosed area is the area that has been enlarged in FIG. 17.
Figure 21:
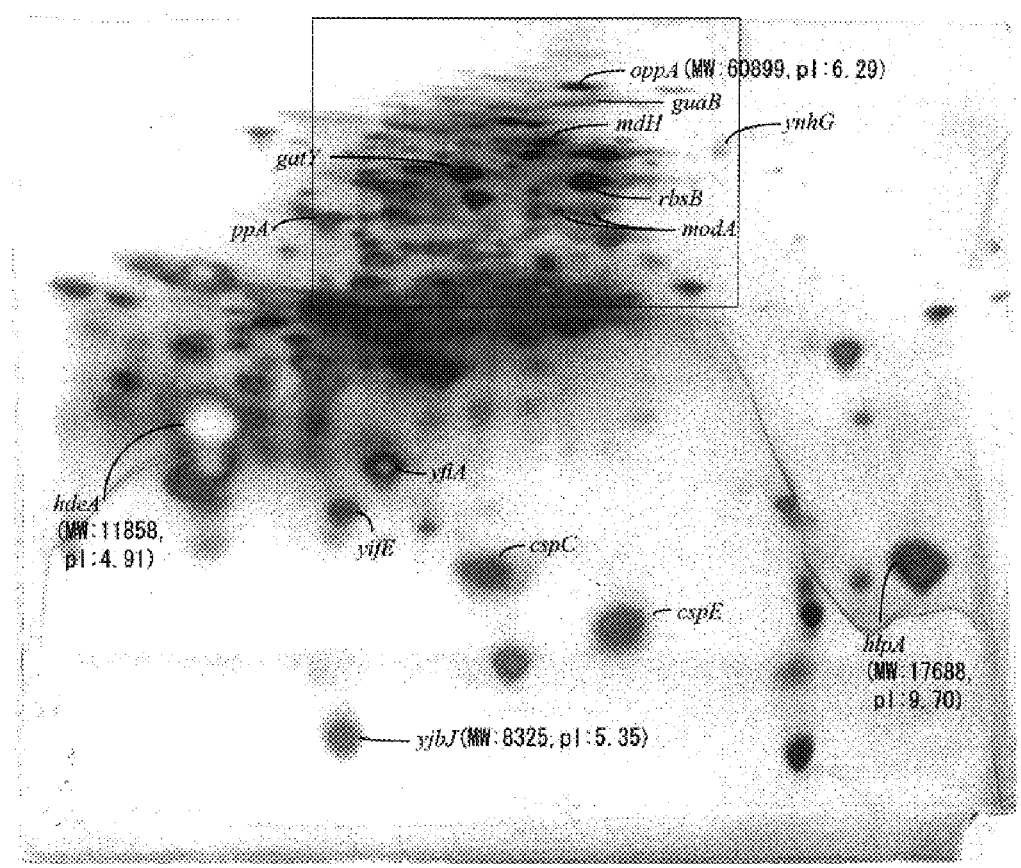
FIG. 21 is a plan view of the two dimensional gel emphasizing the acid region of the PRS protein, and the enclosed area is the area that has been enlarged in FIG. 18.

FIG. 20 shows CD proteins separated by migration conditions that similarly emphasize the basic region. The neutral to weak acid region in FIG. 20 (the enclosed area at the left top) was expanded, and this is FIG. 17. Next, the proteins of the PRS fraction were separated under migration conditions that emphasize the acid region, and this is shown in FIG. 21 (by a double dye of CBB silver). The previous FIG. 18 is an expansion of the enclosed area at the top of FIG. 21. With all of these figures, there are no artificial splitting of the spots such as seen with the immobilized pH gradient method.

Approximately 250 from the CD fraction, 150 from the CR fraction, and 250 from the PRS fraction for a total of approximately 650 spots were detected with CBB dye. The gene identification of these spots is currently in progress. However, currently, of all the spots, approximately 500 spots or almost 80% have had their protein genes identified. With silver dye, there is approximately 20% increase from the CBB dye in spots detected.

Figure 22:
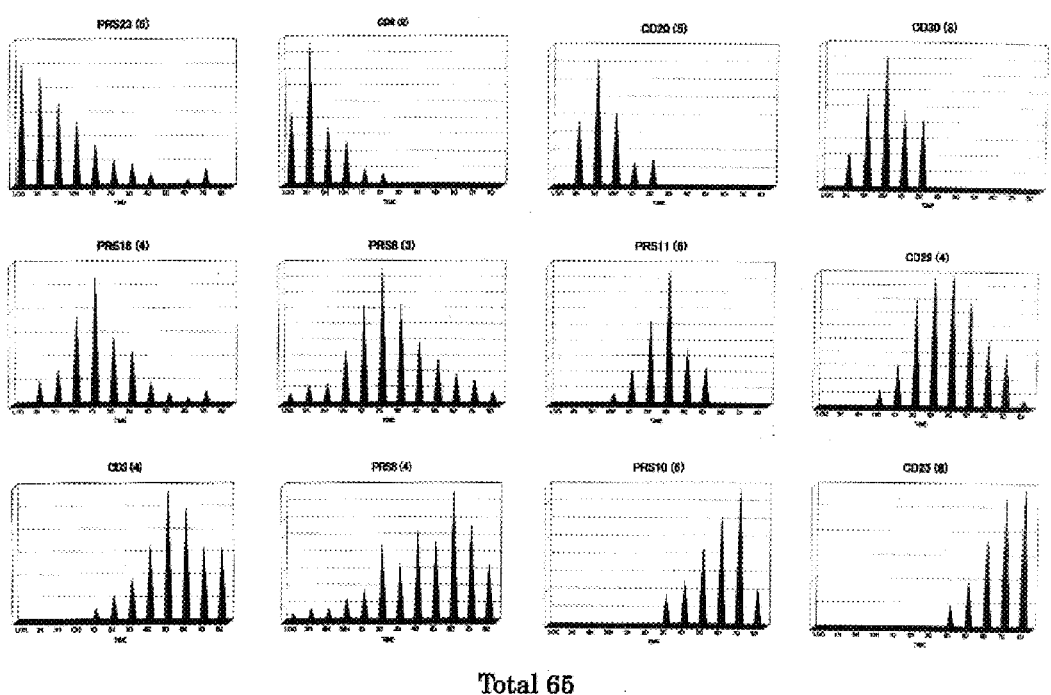
FIG. 22 is a classification drawing in which the unique proteins in the steady period are classified according to the expression time.

Next, we will introduce the results from analysis of changes in the protein composition over time as the E. coli transition in growth stage from logarithmic period to steady period. After approximately 3 hours of logarithmic period, E. coli survive for approximately 7 days in a steady period. Tracking the time of this steady period, proteins were prepared from the CR, PRS, and CD fractions as described above. With the RFHR method, 65 unique proteins for the steady period were detected. FIG. 22 classifies these proteins according to the time they appear. Of the unique proteins discovered for the steady period, approximately ¼ exist over the entire steady period. The remaining ¾ appear for a relatively narrow period during the steady period and then disappear.

Figure 23:
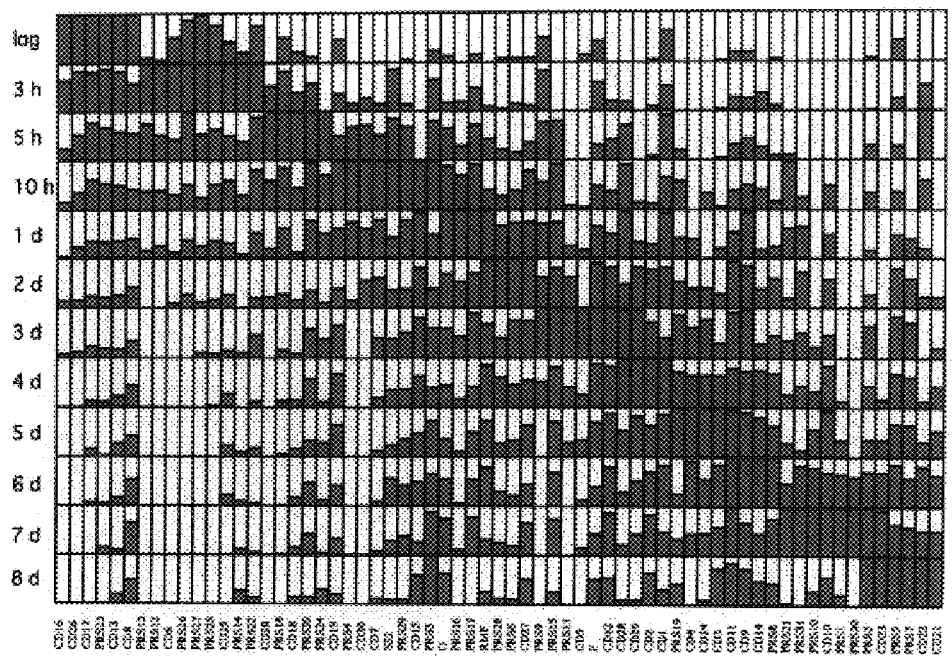
FIG. 23 is a figure showing the transition in the expression of steady period unique proteins. In the lower horizontal direction, the name of the protein spot is listed, and the left vertical direction, the passage of time in the steady period is shown.

FIG. 23 shows the amount of steady period unique protein present in each time period. The amounts have been standardized to the time period showing the maximum value. From this figure, it can be seen that E. coli survive their long steady period by changing their structure moment by moment. Of the 65 spots detected, 39 have had their genes identified. However, approximately half have an unknown function, and these were more often seen in the later period of the steady period.

Experiment 2

In the second experiment, for the creation of the zero-dimension sample gel, electrophoresis of a sample was conducted at a pH of 3.0 in a pre-treatment rod-shaped gel with a buffer solution containing K+ as a leading ion and glutamic acid as a trailing ion. With this, a zero-dimension sample gel in which proteins of all different isoelectric points were concentrated in the negative electrode direction was created. This sample gel fragment was inserted into the first dimension gel at the desired position (position corresponding to the window), and first dimension electrophoresis was conducted. The resulting first dimension gel was placed on the upper end of the second dimension gel, and further electrophoresis was conducted. As a result, two types of protein which were extremely acidic were detected and identified on the two dimensional image.

Experiment 3

In the third experiment, for the creation of the zero-dimension sample gel, electrophoresis of a sample was conducted at a pH of 10.6 in a pre-treatment rod-shaped gel with a buffer solution containing Cl− as a leading ion and arginine as a trailing ion. With this, a zero-dimension sample gel in which proteins with isoelectric points of pH 11 or less were concentrated in the positive electrode direction was created. This sample gel was inserted into the first dimension gel at the desired position (position corresponding to the window), and first dimension electrophoresis was conducted. The resulting first dimension gel was placed on the upper end of the second dimension gel, and further electrophoresis was conducted. As a result, two proteins with extremely high acidity were detected and identified.

It will be appreciated that various modifications to the inventive concepts described herein may be apparent to those skilled in the art without departing from the scope of the present invention as defined by the hereinafter appended claims.

What is claimed is:

1. An electrophoresis apparatus, comprising:
   A gel container forming at least one row of gel chambers;
   A first buffer reservoir and a second buffer reservoir which have container insertion openings, respectively, through the gel chambers of the gel container; and
   A plate-type gel contained in the gel container and being surrounded with non-conductive material plates, an open end of the gel container being laced in a first buffer reservoir and an opposite open end of the gel container being placed in the second buffer reservoir, Wherein the gel container and the first and second buffer reservoirs are interconnected to form a liquid tight sealing structure, The gel container and the first and second buffer reservoirs are immersed in a cooling reservoir in which cooling liquid is maintained at a range of 4-10° C. and is in direct contact with the gel container, and The buffer reservoirs are respectively equipped with electrode outlet conductors for supplying an electrophoresis voltage, wherein said conductors extend from each of the reservoirs and are insulated physically and electrically from the cooling liquid.

2. An electrophoresis apparatus, comprising:

a gel container forming at least one row of gel chambers;

a first buffer reservoir and a second buffer reservoir which have container insertion openings, respectively, through the gel chambers of the gel container; and a plate-type gel contained in the gel container and being surrounded with non-conductive material plates, wherein the gel container is in a vertical structure, an upper open end of the gel container is connected to a first buffer reservoir and a lower open end of the gel container is connected to the second buffer reservoir, the second buffer reservoir has a panel portion which is bent upward from the main area which is in communication with lower end openings of the gel chambers, an upper end of the panel portion provides a single opening for the second buffer reservoir;

with the exception of the upper end of the first buffer reservoir and the upper end of the panel portion of the second buffer reservoir, the apparatus is substantially immersed in cooling liquid, and the buffer reservoirs are respectively equipped with electrode outlet conductors for supplying an electrophoresis voltage, wherein said conductors extend from each of the reservoirs and are insulated physically and electrically from the cooling liquid.

3. An electrophoresis apparatus according to claim 1, wherein the gel container at a middle portion has an opening across the at least one row of gel chambers the middle portion connects to one part of each gel chamber, the opening is configured for inserting a concentrated sample gel piece, and a window cover plate includes a cap member for inserting into and tightly closing the opening after inserting the concentrated sample gel piece.

4. An electrophoresis apparatus according to claim 2, wherein the gel container at a middle portion has an opening across the at least one row of gel chambers, the middle portion connects to one part of each gel chamber, the opening is configured for inserting a concentrated sample gel piece, and a window cover plate includes a cap member for inserting into and tightly closing the opening after inserting the concentrated sample gel piece.

* * * * *